(12) United States Patent
Liu

(10) Patent No.: US 8,999,927 B2
(45) Date of Patent: Apr. 7, 2015

(54) GLIAL CELL LINE-DERIVED NEUROTROPHIC FACTOR (GDNF) COMPOSITIONS AND USE THEREOF

(71) Applicant: The United States of America, as represented by the Secretary, Department of Health and Human Services, Washington, DC (US)

(72) Inventor: Qing-Rong Liu, Perry Hall, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 1 day.

(21) Appl. No.: 13/855,533

(22) Filed: Apr. 2, 2013

(65) Prior Publication Data

US 2013/0261053 A1    Oct. 3, 2013

Related U.S. Application Data

(60) Provisional application No. 61/619,296, filed on Apr. 2, 2012.

(51) Int. Cl.
*C07K 14/47* (2006.01)
*C07K 14/475* (2006.01)
*C07K 16/22* (2006.01)

(52) U.S. Cl.
CPC .............. *C07K 14/47* (2013.01); *C07K 14/475* (2013.01); *C07K 16/22* (2013.01)

(58) Field of Classification Search
CPC ...... C07K 14/47; C07K 14/475; C07K 16/18; C07K 2319/35; C07K 2319/00; C12N 15/113; A61K 38/185; A61K 38/16
USPC ............. 435/320.1, 353, 366; 514/17.7, 17.8, 514/17.9, 21.2, 21.3, 44 R, 6.9; 530/324, 530/350, 387.9; 536/23.5
See application file for complete search history.

(56) References Cited

U.S. PATENT DOCUMENTS

| | | | |
|---|---|---|---|
| 5,731,284 A * | 3/1998 | Williams | 514/8.4 |
| 2003/0050273 A1 | 3/2003 | Ozawa et al. | |
| 2004/0202642 A1 | 10/2004 | Arbischer et al. | |
| 2011/0319476 A1 | 12/2011 | Collard et al. | |

FOREIGN PATENT DOCUMENTS

WO    WO 2010/093906    8/2010

OTHER PUBLICATIONS

Airavaara et al. (J. Biol. Chem. 2011. 286:45093-45102, published online Nov. 11, 2011).*
Bradley et al. (PLoS ONE 5(3):e9753, Mar. 18, 2010).*
Airavaara et al., "Identification of Novel GDNF Isoforms and *cis*-Antisense GDNFOS Gene and Their Regulation in Human Middle Temporal Gyrus of Alzheimer Disease," *J. Biol. Chem.*, vol. 286:45093-45102, 2011.
Biju et al., "Macrophage-Mediated GDNF Delivery Protects Against Dopaminergic Neurodegeneration: A Therapeutic Strategy for Parkinson's Disease," *Mol. Therapy*, vol. 18(8):1536-1544, 2010.
Bradley et al., "Dopamine Neuron Stimulating Actions of GDNF Propetide," *PLos One*, vol. 5:e9752, 2010.
GenBank Accession No. AC008869.5, "Homo sapiens chromosome 5 clone CTD-2194L12, complete sequence," deposited Aug. 3, 1999.
GenBank Accession No. AC108172.1, "Homo sapiens chromosome 5 clone RP11-17171P23," deposited Jan. 26, 2002.
Grimm et al., "Analysis of the Human GDNF Gene Reveals an Inducible Promoter, Three Exons, A Triplet Repeat with the 3'-UTR and Alternative Splice Products," *Hum. Mol. Genet.*, vol. 7(12):1873-1886, 1998.
Konishi et al., "Disruption of Specific GDNF Receptor Subtype Signaling Impairs Cortical Neuronal Survival in Alzheimer's Brains," *Mol. Neurodegeneration*, vol. 7 (Suppl. 1):L26, 2012.
Levy et al., "Therapeutic Potential of Neurotrophic Factors in Neurodegenerative Diseases," *Biodrugs*, vol. 19(2):97-127, 2005.
Modarresi et al., "Inhibition of Natural Antisense Transcripts in vivo Results in Gene-Specific Transcriptional Upregulation," *Nature Biotech.*, pp. 1-9, 2012.

* cited by examiner

*Primary Examiner* — Louise Humphrey
*Assistant Examiner* — Tara Martinez
(74) *Attorney, Agent, or Firm* — Klarquist Sparkman, LLP

(57) ABSTRACT

Described herein is the identification of primate-specific glial cell line-derived neurotrophic factor opposite strand (GDNFOS) transcripts and encoded peptides. In particular embodiments, provided herein are three GDNFOS antisense transcripts, referred to as GDNFOS-1, GDNFOS-2 and GDNFOS-3. The GDNFOS-3 transcript encodes an ORF of 105 amino acids. Compositions comprising the GDNFOS transcripts and peptides are also provided by the present disclosure. Further provided are methods of treating a neurodegenerative or peripheral organ disease in a subject by administering a therapeutically effective amount of the disclosed GDNFOS nucleic acid molecules, peptides or compositions.

21 Claims, 15 Drawing Sheets

FIG. 3

```
    attgacttttaacatggtggctctgtggtgggatgtggggttaacctaacatcattacaa   60
    aatttacaaatcatagttatggtggtttatttggaaatgttttctgtggatgccctgtct  120
    catttattgtatatgaattttttgttatgtttaatctctaggggttggtttggcttgtgact 180
    ctcatttttatttgaaatatttcaaacatacataaaagagtgtatgtccagatgtcatt  240
    tatctagcaaacacatgactctgtagaacagtagttgccaactttatttattaatgtagt  300
    agcggaaccctttttgcaaatggcatgctatgcagaagcccattatataaaacatctcag  360
    agcttctctggttgaagcaaaatggagggcttggagccttcctagattaaacccacctt   420
    ggccaccccttttctacaccacggtagcccttgaatctgctcacccagcctgaaggtctt  480
    gtgagcacatctgaaaagcacagattaagaaccagaaagcaagctaaacacagtgatcag  540
    attagccatagcaggtgatccagtgtccaaacagtaaagcccatccgttttcttcataga  600
    ggagcctctgagattctcattcggaactctgggctcttatgttagccacaattctaacaa  660
    gctttgcaatctggtttctcagtcacggaagaatagaagaacaactcagaggaggaagaa  720
    gtcagacatagccagacacggctgctagcagttccaccaatgaaagaggagaccaggatg  780
    tttaaaacaggcaaacacaaggtgcgaaaaaccagaagcgaaaacttctgaggtcattta  840
    agcaaggactatcgttatccccggaagcagagagaagttcccctttgcccaacatcacact 900
    gcaagcacgtgttggagctgagattcaaacccaggcatccagggtccagggcccatgctt  940
    ttaatatattccatatcttaggagaatttccctatttaaacaataaaagtgcaaaaatc  960
    ttgtggctagccaaaattttcagttgtttggaaaacttatttatccaataagtggaaaac 1020
    tcacttgtcctccaacaattctggataaatgaaagaacgaattgaactgagactggaatc 1080
    cgggtctcccagtactttgtagttcctatccatatggcttgtcaggaaggccacagggag 1140
    gttaactaactctgcgtaaccagaaacaatcccacatcagactgttggcagtgggagtgg 1200
    aacactcagagctgaaccgcatgcaagatggttgcattttcatttgcaatgtcgtcatct 1260
    tcctcatggctaaagaggtattttggagttgacatgaaggctactgtaattttttagaggc 1320
    atttcttctggcctgtatttacatattgtggtagaagagtcagaagacttcaagcttc   1380
    aaaagtgaatcttgttgcgagttacaaaagcaccaccccggtggggtgcagctctcagcAT 1440
    GTGTCACCACAGGCACTGTGATTTCCCTGTCTTCATCCAACTTTGGTTGCTGTTCTTCAT 1500
  1 M  C  H  H  R  H  C  D  F  P  V  F  I  Q  L  W  L  L  F  F
    GCTCAGGAATTCTGCAACTGCTGTAGCTTTTGCTGTTGTTATGTCTGTAGGTATGGACTC 1560
 21 M  L  R  N  S  A  T  A  V  A  F  A  V  V  M  S  V  G  M  D
    ATTTCTACCATTCTGGAATGAAACATTATTTCAAGGGAAGCTTCTCATTGTAAAAGGTCC 1620
 41 S  F  L  P  F  W  N  E  T  L  F  Q  G  K  L  L  I  V  K  G
    ACACATTCAGAAGGAAACTGGGAGTACATTTTCTCATAGGCCTGGAGCATTAACTGACTA 1680
 61 P  H  I  Q  K  E  T  G  S  T  F  S  H  R  P  G  A  L  T  D
    TGCATCTTTCCCCTCAGTGTTGTCATCATGTTGTAAGGGGATGAGTCATGGACAACATTT 1740
 81 Y  A  S  F  P  S  V  L  S  S  C  C  K  G  M  S  H  G  Q  H
    TCACACACATACGTGAggtccattgaccagtctttaggacaactagaaatcttttcttc 1800
101 F  H  T  H  T  *
    tttgttttaaaaaggaagacaagtcaagatacagcaaataaaaatgctcagcacatttgc 1920
    tgaaatcttagcaaaatcaaaaaaaaaaaaaaaaaaaaaaaaa                  1963
```

FIG. 7 signal peptide

```
Ex1_4S   ------------------MKLWDVVAVCLVLLHTASAFPLPA--------------------  24
Ex3_4S   ------------------MKLWDVVAVCLVLLHTASAFPLPA--------------------  24
Ex4S_5   --------------------------------------------------------------
Ex1_4L   ------------------MKLWDVVAVCLVLLHTASAFPLPAGKRPPEAPAEDRSLGRRRA  43
Ex2_4L   MQSLFRSQGRAAGPEFKMKLWDVVAVCLVLLHTASAFPLPAGKRPPEAPAEDRSLGRRRA  60
```
                                              DNSP-11 peptide

```
Ex1_4S   --------ANMPEDYPDQFDDVMDFIQATIKRLKRSPDKQMAVLPRRERNRQAAAANPENS  77
Ex3_4S   --------ANMPEDYPDQFDDVMDFIQATIKRLKRSPDKQMAVLPRRERNRQAAAANPENS  77
Ex4S_5   ---------MPEDYPDQFDDVMDFIQATIKRLKRSPDKQMAVLPRRERNRQAAAANPENS  51
Ex1_4L   PFALSSDSNMPEDYPDQFDDVMDFIQATIKRLKRSPDKQMAVLPRRERNRQAAAANPENS  103
Ex2_4L   PFALSSDSNMPEDYPDQFDDVMDFIQATIKRLKRSPDKQMAVLPRRERNRQAAAANPENS  120
                 ***************************************************
```

```
Ex1_4S   RGKGRRGQRGKNRGCVLTAIHLNVTDLGLGYETKEELIFRYCSGSCDAAETTYDKILKNL  137
Ex3_4S   RGKGRRGQRGKNRGCVLTAIHLNVTDLGLGYETKEELIFRYCSGSCDAAETTYDKILKNL  137
Ex4S_5   RGKGRRGQRGKNRGCVLTAIHLNVTDLGLGYETKEELIFRYCSGSCDAAETTYDKILKNL  111
Ex1_4L   RGKGRRGQRGKNRGCVLTAIHLNVTDLGLGYETKEELIFRYCSGSCDAAETTYDKILKNL  163
Ex2_4L   RGKGRRGQRGKNRGCVLTAIHLNVTDLGLGYETKEELIFRYCSGSCDAAETTYDKILKNL  180
         ************************************************************
```

```
Ex1_4S   SRNRRLVSDKVGQACCRPIAFDDDLSFLDDNLVYHILRKHSAKRCGCI 185  (SEQ ID NO:5)
Ex3_4S   SRNRRLVSDKVGQACCRPIAFDDDLSFLDDNLVYHILRKHSAKRCGCI 185  (SEQ ID NO:6)
Ex4S_5   SRNRRLVSDKVGQACCRPIAFDDDLSFLDDNLVYHILRKHSAKRCGCI 159  (SEQ ID NO:7)
Ex1_4L   SRNRRLVSDKVGQACCRPIAFDDDLSFLDDNLVYHILRKHSAKRCGCI 211  (SEQ ID NO:8)
Ex2_4L   SRNRRLVSDKVGQACCRPIAFDDDLSFLDDNLVYHILRKHSAKRCGCI 228  (SEQ ID NO:9)
         ************************************************
```

| | | | | | | | | | | | | | | |
|---|---|---|---|---|---|---|---|---|---|---|---|---|---|---|
| Human | G | T | G | G | T | C | A | A | T | A | T | G | A | G | G | T |
| Chimp | G | T | G | G | T | C | A | A | T | A | T | G | A | G | G | T |
| Gorilla | G | T | G | G | T | C | A | A | T | A | T | G | A | A | G | T |
| Orangutan | G | T | G | A | T | C | A | A | T | A | T | G | A | A | G | T |
| Rhesus | G | T | T | G | T | C | A | A | T | A | T | G | A | A | G | T |
| Baboon | G | T | T | G | T | C | A | A | T | A | T | G | A | A | G | T |
| Marmoset | G | T | G | G | T | C | A | A | T | A | T | G | A | A | G | T |
| Tarsier | G | T | G | G | T | C | A | A | T | G | T | G | A | A | T | T |
| Mouse_lemur | G | T | A | G | T | C | A | A | T | A | T | G | A | A | G | T |
| Bushbaby | A | T | A | G | C | T | A | A | T | A | T | G | A | A | G | T |
| Tree_shrew | G | T | G | G | C | C | A | A | G | A | T | G | A | A | G | A | T |
| Mouse | G | T | G | G | T | T | G | A | C | A | G | A | A | T | G | A |
| Rat | | | | | | | | | | | | | | | | |
| Kangaroo_rat | G | T | C | C | T | C | A | A | C | | | | | | | |
| Guinea_pig | | | | | | | | | | | | | | | | |
| Squirrel | | | | | | | | | | | | | | | | |
| Rabbit | C | T | G | G | C | C | A | A | T | A | C | A | A | T | G | T |
| Pika | | | | | | | | | | | | | | | | |
| Alpaca | | | | | | | | | | | | | | | | |
| Dolphin | G | T | G | A | C | C | A | A | T | A | T | G | A | T | G | T |
| Cow | G | T | G | A | C | C | A | A | T | A | T | G | A | A | T | G | T |
| Horse | G | T | G | G | C | C | A | A | T | A | A | A | A | T | A | T |
| Cat | G | T | G | A | C | C | A | A | T | A | T | G | A | A | T | G | T |
| Dog | | | | | | | | | | | | | | | | |
| Microbat | G | T | G | G | C | C | A | A | T | A | T | G | A | A | T | G | C |
| Megabat | G | T | G | G | C | C | A | G | T | A | T | G | A | A | T | A | T |
| Hedgehog | | | | | | | | | | | | | | | | |
| Shrew | | | | | | | | | | | | | | | | |
| Elephant | C | T | G | G | C | C | A | A | C | G | T | A | A | A | T | G | T |
| Rock_hyrax | C | T | G | G | C | C | A | A | T | G | G | G | A | A | G | A |
| Tenrec | C | T | G | G | C | C | A | A | T | G | T | G | A | T | G | T |
| Armadillo | | | | | | | | | | | | | | | | |
| Sloth | | | | | | | | | | | | | | | | |
| Wallaby | | | | | | | | | | | | | | | | |

| | | | | | | | | | | | | | | | | | | |
|---|---|---|---|---|---|---|---|---|---|---|---|---|---|---|---|---|---|---|
| Human | A | C | T | T | C | T | G | A | G | G | T | C | A | T | T | A | A | G | G | T |
| Chimp | A | C | T | T | C | T | G | A | G | G | T | C | A | T | T | A | A | G | G | T |
| Gorilla | A | C | T | T | C | T | G | A | G | G | T | C | A | T | T | A | A | G | G | T |
| Orangutan | A | C | T | T | C | T | G | A | G | G | T | C | A | T | T | A | A | G | G | T |
| Rhesus | A | C | T | T | C | T | G | A | G | G | T | C | A | T | T | A | A | G | G | T |
| Baboon | A | C | T | T | C | T | G | A | G | G | T | C | G | T | T | A | A | G | G | T |
| Marmoset | A | A | T | T | C | T | G | A | G | G | T | C | A | T | T | A | A | G | G | T |
| Tarsier | C | T | T | T | C | T | G | A | G | G | T | T | A | T | C | T | A | A | G | G | G |
| Mouse_lemur | C | C | T | T | C | T | G | A | G | G | C | C | A | T | T | T | A | C | G | G | T |
| Bushbaby | | | | | | | | | | | | | | | | | | | | | |
| Tree_shrew | | | | | | | | | | | | | | | | | | | | | |
| Mouse | C | C | C | T | T | G | G | A | G | G | T | T | G | C | T | T | C | A | G | G | T |
| Rat | C | C | T | T | T | G | G | A | G | G | T | T | G | C | T | T | C | A | G | A | T |
| Kangaroo_rat | | | | | | | | | | | | | | | | | | | | | |
| Guinea_pig | | | | | | | | | | | | | | | | | A | A | G | G | T |
| Squirrel | T | C | T | T | C | A | G | A | G | G | T | C | A | T | T | A | A | G | G | T |
| Rabbit | C | T | T | T | C | T | G | A | G | G | T | C | A | T | T | A | A | G | G | T |
| Pika | T | G | T | T | C | T | G | | G | G | T | C | A | T | T | A | A | A | G | T |
| Alpaca | C | C | T | T | C | T | G | A | G | G | T | C | T | T | T | A | G | G | G | T |
| Dolphin | C | C | T | T | C | T | G | A | G | G | T | C | A | T | T | A | G | G | G | T |
| Cow | C | C | T | T | C | T | G | A | G | G | T | C | A | T | A | T | A | G | G | G | T |
| Horse | C | C | T | C | C | T | G | A | G | G | T | C | A | T | T | A | G | G | G | T |
| Cat | C | C | T | T | C | T | G | A | G | G | T | C | A | T | T | A | G | G | G | T |
| Dog | C | C | T | T | C | T | G | A | A | G | T | C | A | T | T | G | G | G | G | T |
| Microbat | | | | | | | | | | | | | | | | | | | | | |
| Megabat | C | C | T | T | T | G | A | G | G | T | C | A | T | T | C | A | G | G | G | T |
| Hedgehog | | | | | | | | | | | | | | | | | | | | | |
| Shrew | C | C | A | T | C | T | G | A | G | A | T | C | A | T | T | C | A | G | A | G | C |
| Elephant | C | C | T | T | C | T | G | A | G | G | T | C | A | T | T | A | G | G | G | T |
| Rock_hyrax | C | C | T | T | C | T | G | A | G | G | T | C | T | T | C | T | A | G | G | G | T |
| Tenrec | | | | | | | | | | | | | | | | | | | | | |
| Armadillo | C | C | T | T | C | G | G | A | G | G | C | C | A | T | T | A | G | T | T |
| Sloth | | | | | | | | | | | | | | | | | | | | | |
| Wallaby | | | | | | | | | | | | | | | | | | | | | |
| Opossum | | | | | | | | | | | | | | | | | | | | | |

FIG. 11E

| | | | | | | | | | | | | |
|---|---|---|---|---|---|---|---|---|---|---|---|---|
| Human | T | C | T | A | C | T | T | T | C | T | G | A | A | G |
| Chimp | T | C | T | A | C | T | T | T | C | T | G | A | A | G |
| Gorilla | T | C | T | A | C | T | T | T | C | T | G | A | A | G |
| Orangutan | T | C | T | A | C | T | T | T | C | T | G | A | A | G |
| Rhesus | T | C | T | A | C | T | T | T | C | T | G | A | A | G |
| Baboon | T | C | T | A | C | T | T | T | C | T | G | A | A | G |
| Marmoset | T | C | T | - | C | T | T | T | A | C | G | A | A | G |
| Tarsier | T | C | T | C | C | T | T | T | A | T | G | A | A | G |
| Mouse_lemur | T | C | C | A | C | T | T | T | A | T | G | A | A | G |
| Bushbaby | T | C | T | G | C | T | T | T | A | T | G | A | A | G |
| Tree_shrew | C | C | A | A | T | T | T | T | A | T | A | G | A | A |
| Mouse | C | C | T | A | T | T | T | T | A | T | G | A | A | G |
| Rat | C | C | T | G | T | T | T | T | A | C | A | A | A | G |
| Kangaroo_rat | - | T | G | A | C | T | T | T | A | T | G | G | A | A |
| Guinea_pig | - | C | T | A | C | T | T | T | G | T | A | A | A | G |
| Squirrel | C | T | T | G | C | T | T | T | G | T | G | A | A | G |
| Rabbit | C | C | T | A | C | T | T | T | A | T | C | A | G | G |
| Pika | T | C | T | A | C | T | T | T | A | T | C | C | A | G |
| Alpaca | C | T | G | A | C | T | T | T | A | T | G | G | A | G |
| Dolphin | C | C | T | A | G | T | T | T | A | T | G | A | A | G |
| Cow | C | C | T | A | C | T | T | T | A | T | G | A | A | G |
| Horse | C | T | T | A | C | T | T | T | A | T | G | A | A | G |
| Cat | C | C | T | A | - | T | T | T | A | T | G | A | A | G |
| Dog | C | C | T | A | T | T | T | T | A | C | G | A | A | G |
| Microbat | - | - | - | - | - | - | - | - | - | - | - | - | - | - |
| Megabat | C | C | T | A | C | T | T | T | A | T | G | A | G | G |
| Hedgehog | - | - | - | - | - | - | - | - | - | - | - | - | - | - |
| Shrew | C | G | G | C | C | T | T | T | T | T | A | A | A | G |
| Elephant | C | T | T | A | C | T | T | T | T | C | G | A | A | G |
| Rock_hyrax | C | T | T | A | C | T | T | T | T | T | G | A | A | G |
| Tenrec | C | C | T | A | C | T | T | T | T | T | G | A | A | A |
| Armadillo | - | - | - | - | - | - | - | - | - | - | - | - | - | - |
| Sloth | - | - | - | - | - | - | - | - | - | - | - | - | - | - |
| Wallaby | | | | | | | | | | | | | | |

SEQUENCE LISTING

```
<160> NUMBER OF SEQ ID NOS: 45

<210> SEQ ID NO 1
<211> LENGTH: 618
<212> TYPE: DNA
<213> ORGANISM: Homo sapiens

<400> SEQUENCE: 1
agcgccgggc tttcctcgcg cctgtcgaag gccggccttc ccgctcgggt gtctcgccct        60
ctcgcttctc cgcagggcag gaggcagtgg cgagaaaagg agctgccggc cggagttcta       120
gcaccgagaa ggagagtact ggaatacctg agttttggct gggcacagaa ctgtctggaa       180
tacagactgc aattcccagc cttctgtgca gttctgtgtg gccatgtgac taagttgtgg       240
tcaatatgag tcacggaaga atagaagaac aactcagagg aggaagaagt cagacatagc       300
cagacacggc tgctagcagt tccaccaatg aaagaggaga ccaggatgtt taaaacaggc       360
aaacacaagg tgcgaaaaac cagaagcgaa aacttctgag gtcatttaag caaggactat       420
cgttatcccc ggaagcagag agaagttccc tttgcccaac atcacactgc aagcacgtgt       480
tggagctgag attcaaaccc aggcatccag ggtccagggc ccatgctctt aatatattcc       540
atatcttagg agaatttccc ctatttaaac aataaaagtg caaaaatctt gtggctagcc       600
aaaaaaaaaa aaaaaaaa                                                    618
```

<210> SEQ ID NO 2
<211> LENGTH: 2944
<212> TYPE: DNA
<213> ORGANISM: Homo sapiens

<400> SEQUENCE: 2

| | | | | | |
|---|---|---|---|---|---|
| attcccttca | gcttcaggag | tgagttgatt | attcacatgt | tcttttagg gggtttaagc | 60 |
| tgctagtcct | taaagaatag | atgctgaagg | ttgtcattga | ttcctctttc cttcctccca | 120 |
| cgtctgctct | gggccttctc | attgatgtag | tatcttaggt | tacttccaaa ataatttgag | 180 |
| aaatggattt | atagaagaag | ctagcttttcc | agtagaaaag | tttagatgac aagattaatg | 240 |
| tgataagaac | taagaaagcc | cttcctagtt | ttcattgaaa | atgtgttttt aatgcccaga | 300 |
| ggtgcccagt | caaaaaggaa | atattacaga | aggattattt | tcatcagcag agttcttggg | 360 |
| cattgcaagt | tccagtgtaa | ttagggaaat | cacatgcgag | tacatcaata cacttcagat | 420 |
| gccaatacat | tgggcttaat | gaggacaaca | agcctgcttt | tattagggga ttgaataaaa | 480 |
| gtgaaaggag | ttcttgaaaa | gaattggtaa | ttttggatgg | gataattcat cacttcactc | 540 |
| cagatcagtt | tttcacagta | agaagtgctg | gctcttcaga | aaatttggca taaccaaagt | 600 |
| ttattgtcac | tatctcctcc | ttctcacatt | gtcctttgtc | gcaccccag caggtccaca | 660 |
| gtgatcctgc | gggccacccc | catggaccct | gcccgttttc | ttccatcggg ggctatctta | 720 |
| cgtcagtctt | tcaaggtctc | ctcagtaatg | caggccagtt | ggattttttgc tttctttttcc | 780 |
| cagaggacaa | ttcagcctca | gcgtcttagt | ctaaaaggat | tcatgcaagc gtgtcagatg | 840 |
| ttttattagg | ctaaggggga | ggtattttgg | gttgtggga | gcacttactg caaccctgta | 900 |
| tgaaattccc | tactcagtga | tgttcaggct | gcacgggcca | acatggaaag ggcttaaggg | 960 |
| agatgacaaa | aacaaaatct | cttcttccac | aaagattttc | agttgatcaa ttttgttact | 1020 |
| tttttgtgat | gaaactatct | gcactgcagc | taatgatttt | tttctgaagg tggaaaaggt | 1080 |
| aggagcaaca | gctttcagtt | ctaaggatac | attctgttga | ccttcataag ccctaggaac | 1140 |
| tagagggca | agattgagga | ggaaatagag | aaaataattt | gctctatagt attttcccc | 1200 |
| tgagctgcca | tctgggctt | tcagagctta | gcactgcact | cttgcaatgt tgcacacacc | 1260 |
| acaggagcaa | tatcaagaga | tgtcaaacat | gagtggtatt | ggtcactgga aacagcagat | 1320 |
| tccaaatagc | tgtctcacca | gactattctt | tcagaagatt | catttgtgcc aactacttct | 1380 |
| ttgtcatgga | tccttcctgg | ttctgcaaca | cagatgtgga | aagtgaagag aacacgtcat | 1440 |
| ggaattccat | ttctaagagt | ggaaaatata | caatttacca | tgggatgttt aagatattaa | 1500 |
| tatattgttc | accatgtgta | tccagagctt | tagtagaagt | aggttaaaag agccgtgcat | 1560 |
| gtatacacgg | tgctcctcat | tgtcaaacgc | tgaagcctgt | tacaggctgg gtttggggc | 1620 |
| tgggggtact | tacgggacaa | agtctgactc | tcggtctgta | ggctgagtgc cttcttagtg | 1680 |
| tgttgggact | cagcatgtat | tcaccccatc | tgtactcaca | agcctaattc attaatcagg | 1740 |
| atgacttact | gggctgtgag | ccctttgagg | acaggaccttt | gtacctttat cttgtgcctc | 1800 |
| tcatgcctag | catagcacca | ggcatgtaac | acgttctttt | taaaaaagtg ttttacagct | 1860 |
| ttatcaaggc | atacatgatg | tcagatcaac | tgcatgtgtt | taaagttta cacttgatga | 1920 |
| gttttgatat | atgtctatac | ccgtgaaacc | atcactgcaa | tcaagataat aaacgcattc | 1980 |
| atccacccta | aagtttctcg | tgtcccttttg | caagccaccc ccttcctcc | cattgttccc | 2040 |
| agacaaccac | tattctgctt | tctgtcactg | cagatgagtt | tgtgtttttct ggaatttat | 2100 |

| | |
|---|---:|
| ataagtggaa tcatacaaca tgtactctgt tttttctggc tgttttcact cagcataatt | 2160 |
| ttctcaagat tcattgaagt tttatatatt aatagtttgc tacatttcat tgctgaatag | 2220 |
| tattccattg tataaatcat aataggcacc taacaagtgt tgtggctttt acactgactt | 2280 |
| gaaaattaat tttaagaat ataattgggc aaaaagtgga caatgggata ccactctatt | 2340 |
| cttggtgagt gggttcactc aggaagtgga aataagaatc aggagataat tggcatggt | 2400 |
| agagactttt gttgtcatcc aatatctatt tttccttctt tcttagtact ggaatacctg | 2460 |
| agttttggct gggcacagaa ctgtctggaa tacagactgc aattcccagc cttctgtgca | 2520 |
| gttctgtgtg gccatgtgac taagttgtgg tcaatgtgag tcacggaaga atagaagaac | 2580 |
| aactcagagg aggaagaagt cagacatagc cagacacggc tgctagcagt tccaccaatg | 2640 |
| aaagaggaga ccaggatgtt taaaacaggc aaacacaagg tgcgaaaaac cagaagcgaa | 2700 |
| aacttctgag gtcatttaag caaggactat cgttatcccc ggaagcagag agaagttccc | 2760 |
| tttgcccaac atcacactgc aagcacgtgt tggagctgag attcaaaccc aggcatccag | 2820 |
| ggtccagggc ccatgctctt aatatattcc atatcttagg agaatttccc ctatttaaac | 2880 |
| aataaaagtg caaaatctt gtggctagcc aaaaaaaaaa aaaaaaaaa aaaaaaaaa | 2940 |
| aaaa | 2944 |

<210> SEQ ID NO 3
<211> LENGTH: 1963
<212> TYPE: DNA
<213> ORGANISM: Homo sapiens

<400> SEQUENCE: 3

| | |
|---|---:|
| attgactttt aacatggtgg ctctgtggtg ggatgtgggg ttaacctaac atcattacaa | 60 |
| aatttacaaa tcatagttat ggtggtttat ttggaaatgt tttctgtgga tgccctgtct | 120 |
| catttattgt atatgaattt ttgttatgtt taatctctag ggttggtttg gcttgtgact | 180 |
| ctcattttt atttgaaata tttcaaacat acataaaaga gtgtatgtcc agatgtcatt | 240 |
| tatctagcaa acacatgact ctgtagaaca gtagttgcca actttattta ttaatgtagt | 300 |
| agcggaaccc ttttgcaaa tggcatgcta tgcagaagcc cattatataa aacatctcag | 360 |
| agcttctctg gttgaagcaa aatggagggc ttggagcctt cctagattaa accccacctt | 420 |
| ggccacccct ttctacacca cggtagcccc ttgaatctgc tcacccagcc tgaaggtctt | 480 |
| gtgagcacat ctgaaaagca cagattaaga accagaaagc aagctaaaca cagtgatcag | 540 |
| attagccata gcaggtgatc cagtgtccaa acagtaaagc ccatccgttt tcttcataga | 600 |
| ggagcctctg agattctcat tcggaactct gggctcttat gttagccaca attctaacaa | 660 |
| gctttgcaat ctggtttctc agtcacggaa gaatagaaga acaactcaga ggaggaagaa | 720 |
| gtcagacata gccagacacg gctgctagca gttccaccaa tgaaagagga gaccaggatg | 780 |
| tttaaaacag gcaaacacaa ggtgcgaaaa accagaagcg aaaacttctg aggtcatta | 840 |
| agcaaggact atcgttatcc ccggaagcag agagaagttc cctttgccca acatcacact | 900 |
| gcaagcacgt gttggagctg agattcaaac ccaggcatcc agggtccagg gcccatgctt | 960 |
| ttaatatatt ccatatctta ggagaatttc ccctatttaa acaataaaag tgcaaaaatc | 1020 |
| ttgtggctag ccaaaatttt cagttgtttg gaaaacttat ttatccaata agtggaaaac | 1080 |
| tcacttgtcc tccaacaatt ctggataaat gaaagaacga attgaactga gactggaatc | 1140 |
| cgggtctccc agtactttgt agttcctatc catatggctt gtcaggaagg ccacaggag | 1200 |
| gttaactaac tctgcgtaac cagaaacaat cccacatcag actgttggca gtgggagtgg | 1260 |

-continued

```
aacactcaga gctgaaccgc atgcaagatg gttgcatttt catttgcaat gtcgtcatct      1320
tcctcatggc taaagaggta ttttggagtt gacatgaagg ctactgtaat ttttagaggc      1380
attttctttc tggcctgtat ttacatattg tggtagaaga gtcagaagac ttcaagcttc      1440
aaaagtgaat cttgttgcga gttacaaaag caccacccgg tggggtgcag ctctcagcat      1500
gtgtcaccac aggcactgtg atttccctgt cttcatccaa ctttggttgc tgttcttcat      1560
gctcaggaat tctgcaactg ctgtagcttt tgctgttgtt atgtctgtag gtatggactc      1620
atttctacca ttctggaatg aaacattatt tcaagggaag cttctcattg taaaaggtcc      1680
acacattcag aaggaaactg ggagtacatt ttctcatagg cctggagcat taactgacta      1740
tgcatctttc ccctcagtgt tgtcatcatg ttgtaagggg atgagtcatg gacaacattt      1800
tcacacacat acgtgaggtc cattgaccag tctttaggac aactagaaat cttttctttc      1860
tttgttttaa aaggaagac aagtcaagat acagcaaata aaaatgctca gcacatttgc      1920
tgaaatctta gcaaaatcaa aaaaaaaaaa aaaaaaaaa aaa                         1963
```

<210> SEQ ID NO 4
<211> LENGTH: 105
<212> TYPE: PRT
<213> ORGANISM: Homo sapiens

<400> SEQUENCE: 4

```
Met Cys His His Arg His Cys Asp Phe Pro Val Phe Ile Gln Leu Trp
1               5                   10                  15

Leu Leu Phe Phe Met Leu Arg Asn Ser Ala Thr Ala Val Ala Phe Ala
            20                  25                  30

Val Val Met Ser Val Gly Met Asp Ser Phe Leu Pro Phe Trp Asn Glu
        35                  40                  45

Thr Leu Phe Gln Gly Lys Leu Leu Ile Val Lys Gly Pro His Ile Gln
    50                  55                  60

Lys Glu Thr Gly Ser Thr Phe Ser His Arg Pro Gly Ala Leu Thr Asp
65                  70                  75                  80

Tyr Ala Ser Phe Pro Ser Val Leu Ser Ser Cys Cys Lys Gly Met Ser
                85                  90                  95

His Gly Gln His Phe His Thr His Thr
            100                 105
```

<210> SEQ ID NO 5
<211> LENGTH: 185
<212> TYPE: PRT
<213> ORGANISM: Homo sapiens

<400> SEQUENCE: 5

```
Met Lys Leu Trp Asp Val Val Ala Val Cys Leu Val Leu Leu His Thr
1               5                   10                  15

Ala Ser Ala Phe Pro Leu Pro Ala Ala Asn Met Pro Glu Asp Tyr Pro
            20                  25                  30

Asp Gln Phe Asp Asp Val Met Asp Phe Ile Gln Ala Thr Ile Lys Arg
        35                  40                  45

Leu Lys Arg Ser Pro Asp Lys Gln Met Ala Val Leu Pro Arg Arg Glu
    50                  55                  60

Arg Asn Arg Gln Ala Ala Ala Ala Asn Pro Glu Asn Ser Arg Gly Lys
65                  70                  75                  80

Gly Arg Arg Gly Gln Arg Gly Lys Asn Arg Gly Cys Val Leu Thr Ala
                85                  90                  95
```

```
Ile His Leu Asn Val Thr Asp Leu Gly Leu Gly Tyr Glu Thr Lys Glu
            100                 105                 110

Glu Leu Ile Phe Arg Tyr Cys Ser Gly Ser Cys Asp Ala Ala Glu Thr
            115                 120                 125

Thr Tyr Asp Lys Ile Leu Lys Asn Leu Ser Arg Asn Arg Arg Leu Val
            130                 135                 140

Ser Asp Lys Val Gly Gln Ala Cys Cys Arg Pro Ile Ala Phe Asp Asp
145                 150                 155                 160

Asp Leu Ser Phe Leu Asp Asp Asn Leu Val Tyr His Ile Leu Arg Lys
                165                 170                 175

His Ser Ala Lys Arg Cys Gly Cys Ile
            180                 185
```

```
<210> SEQ ID NO 6
<211> LENGTH: 185
<212> TYPE: PRT
<213> ORGANISM: Homo sapiens

<400> SEQUENCE: 6

Met Lys Leu Trp Asp Val Val Ala Val Cys Leu Val Leu Leu His Thr
1               5                   10                  15

Ala Ser Ala Phe Pro Leu Pro Ala Ala Asn Met Pro Glu Asp Tyr Pro
            20                  25                  30

Asp Gln Phe Asp Asp Val Met Asp Phe Ile Gln Ala Thr Ile Lys Arg
            35                  40                  45

Leu Lys Arg Ser Pro Asp Lys Gln Met Ala Val Leu Pro Arg Arg Glu
50                  55                  60

Arg Asn Arg Gln Ala Ala Ala Ala Asn Pro Glu Asn Ser Arg Gly Lys
65                  70                  75                  80

Gly Arg Arg Gly Gln Arg Gly Lys Asn Arg Gly Cys Val Leu Thr Ala
            85                  90                  95

Ile His Leu Asn Val Thr Asp Leu Gly Leu Gly Tyr Glu Thr Lys Glu
            100                 105                 110

Glu Leu Ile Phe Arg Tyr Cys Ser Gly Ser Cys Asp Ala Ala Glu Thr
            115                 120                 125

Thr Tyr Asp Lys Ile Leu Lys Asn Leu Ser Arg Asn Arg Arg Leu Val
            130                 135                 140

Ser Asp Lys Val Gly Gln Ala Cys Cys Arg Pro Ile Ala Phe Asp Asp
145                 150                 155                 160

Asp Leu Ser Phe Leu Asp Asp Asn Leu Val Tyr His Ile Leu Arg Lys
                165                 170                 175

His Ser Ala Lys Arg Cys Gly Cys Ile
            180                 185
```

```
<210> SEQ ID NO 7
<211> LENGTH: 159
<212> TYPE: PRT
<213> ORGANISM: Homo sapiens

<400> SEQUENCE: 7

Met Pro Glu Asp Tyr Pro Asp Gln Phe Asp Asp Val Met Asp Phe Ile
1               5                   10                  15

Gln Ala Thr Ile Lys Arg Leu Lys Arg Ser Pro Asp Lys Gln Met Ala
            20                  25                  30

Val Leu Pro Arg Arg Glu Arg Asn Arg Gln Ala Ala Ala Ala Asn Pro
            35                  40                  45
```

```
Glu Asn Ser Arg Gly Lys Gly Arg Gly Gln Arg Gly Lys Asn Arg
 50                  55                  60

Gly Cys Val Leu Thr Ala Ile His Leu Asn Val Thr Asp Leu Gly Leu
 65                  70                  75                  80

Gly Tyr Glu Thr Lys Glu Glu Leu Ile Phe Arg Tyr Cys Ser Gly Ser
                     85                  90                  95

Cys Asp Ala Ala Glu Thr Thr Tyr Asp Lys Ile Leu Lys Asn Leu Ser
                100                 105                 110

Arg Asn Arg Arg Leu Val Ser Asp Lys Val Gly Gln Ala Cys Cys Arg
                115                 120                 125

Pro Ile Ala Phe Asp Asp Leu Ser Phe Leu Asp Asp Asn Leu Val
130                 135                 140

Tyr His Ile Leu Arg Lys His Ser Ala Lys Arg Cys Gly Cys Ile
145                 150                 155
```

<210> SEQ ID NO 8
<211> LENGTH: 211
<212> TYPE: PRT
<213> ORGANISM: Homo sapiens

<400> SEQUENCE: 8

```
Met Lys Leu Trp Asp Val Val Ala Val Cys Leu Val Leu Leu His Thr
 1               5                  10                  15

Ala Ser Ala Phe Pro Leu Pro Ala Gly Lys Arg Pro Pro Glu Ala Pro
                 20                  25                  30

Ala Glu Asp Arg Ser Leu Gly Arg Arg Arg Ala Pro Phe Ala Leu Ser
                 35                  40                  45

Ser Asp Ser Asn Met Pro Glu Asp Tyr Pro Asp Gln Phe Asp Asp Val
 50                  55                  60

Met Asp Phe Ile Gln Ala Thr Ile Lys Arg Leu Lys Arg Ser Pro Asp
 65                  70                  75                  80

Lys Gln Met Ala Val Leu Pro Arg Arg Glu Arg Asn Arg Gln Ala Ala
                 85                  90                  95

Ala Ala Asn Pro Glu Asn Ser Arg Gly Lys Gly Arg Arg Gly Gln Arg
                100                 105                 110

Gly Lys Asn Arg Gly Cys Val Leu Thr Ala Ile His Leu Asn Val Thr
                115                 120                 125

Asp Leu Gly Leu Gly Tyr Glu Thr Lys Glu Glu Leu Ile Phe Arg Tyr
130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Leu Ser Phe Leu Asp
                180                 185                 190

Asp Asn Leu Val Tyr His Ile Leu Arg Lys His Ser Ala Lys Arg Cys
                195                 200                 205

Gly Cys Ile
210
```

<210> SEQ ID NO 9
<211> LENGTH: 228
<212> TYPE: PRT
<213> ORGANISM: Homo sapiens

<400> SEQUENCE: 9

```
Met Gln Ser Leu Pro Asn Ser Asn Gly Ala Ala Gly Arg Asp Phe
1               5                   10                  15

Lys Met Lys Leu Trp Asp Val Val Ala Val Cys Leu Val Leu Leu His
            20                  25                  30

Thr Ala Ser Ala Phe Pro Leu Pro Ala Gly Lys Arg Pro Pro Glu Ala
                35                  40                  45

Pro Ala Glu Asp Arg Ser Leu Gly Arg Arg Arg Ala Pro Phe Ala Leu
50                  55                  60

Ser Ser Asp Ser Asn Met Pro Glu Asp Tyr Pro Asp Gln Phe Asp Asp
65                  70                  75                  80

Val Met Asp Phe Ile Gln Ala Thr Ile Lys Arg Leu Lys Arg Ser Pro
                85                  90                  95

Asp Lys Gln Met Ala Val Leu Pro Arg Arg Glu Arg Asn Arg Gln Ala
                100                 105                 110

Ala Ala Ala Asn Pro Glu Asn Ser Arg Gly Lys Gly Arg Arg Gly Gln
            115                 120                 125

Arg Gly Lys Asn Arg Gly Cys Val Leu Thr Ala Ile His Leu Asn Val
            130                 135                 140

Thr Asp Leu Gly Leu Gly Tyr Glu Thr Lys Glu Glu Leu Ile Phe Arg
145                 150                 155                 160

Tyr Cys Ser Gly Ser Cys Asp Ala Ala Glu Thr Thr Tyr Asp Lys Ile
                165                 170                 175

Leu Lys Asn Leu Ser Arg Asn Arg Arg Leu Val Ser Asp Lys Val Gly
                180                 185                 190

Gln Ala Cys Cys Arg Pro Ile Ala Phe Asp Asp Asp Leu Ser Phe Leu
            195                 200                 205

Asp Asp Asn Leu Val Tyr His Ile Leu Arg Lys His Ser Ala Lys Arg
210                 215                 220

Cys Gly Cys Ile
225

<210> SEQ ID NO 10
<211> LENGTH: 13
<212> TYPE: PRT
<213> ORGANISM: Homo sapiens

<400> SEQUENCE: 10

Cys Lys Gly Met Ser His Gly Gln His Phe Thr His Thr
1               5                   10

<210> SEQ ID NO 11
<211> LENGTH: 17
<212> TYPE: PRT
<213> ORGANISM: Homo sapiens

<400> SEQUENCE: 11

Met Gln Ser Leu Pro Asn Ser Asn Gly Ala Ala Gly Arg Asp Phe
1               5                   10                  15

Lys

<210> SEQ ID NO 12
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 12
```
atccgaggtg ccgcc                                                        15

<210> SEQ ID NO 13
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 13
cacctggagt taatgtccaa cct                                               23

<210> SEQ ID NO 14
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 14
cgacatccca taacttcatc ttaaag                                            26

<210> SEQ ID NO 15
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 15
aaaactttca agacaaatgc agt                                               23

<210> SEQ ID NO 16
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 16
ttcgggtata ccacggagga t                                                 21

<210> SEQ ID NO 17
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 17
cggcaccatt gctgttagg                                                    19

<210> SEQ ID NO 18
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 18
caggctgggt gccg                                                         14

<210> SEQ ID NO 19
<211> LENGTH: 24
<212> TYPE: DNA

```
<213> ORGANISM: Artificial Sequence
<220> FEATURE:
<223> OTHER INFORMATION: Synthetic polynucleotide

<400> SEQUENCE: 19
tgctctcgca acagaatacc tatt                                          24

<210> SEQ ID NO 20
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 20
cgacatccca taacttcatc ttaaag                                        26

<210> SEQ ID NO 21
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 21
atgtagccga gacatt                                                   16

<210> SEQ ID NO 22
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 22
ggcacaggaa gatgacttga tg                                            22

<210> SEQ ID NO 23
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 23
tcctctggca tatttgctct tg                                            22

<210> SEQ ID NO 24
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 24
tcctgatcag ttcgatgat                                                19

<210> SEQ ID NO 25
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 25
agtgactcaa atatgccaga ggatt                                         25
```

<210> SEQ ID NO 26
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 26 tcagtcttttt aatggtggct tgaa                                           24

<210> SEQ ID NO 27
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 27
attatcctga tcagttcgat g                                               21

<210> SEQ ID NO 28
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 28
cccgccgcaa atatgc                                                     16

<210> SEQ ID NO 29
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 29 tcagtcttttt aatggtggct tgaa                                           24

<210> SEQ ID NO 30
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 30
cgagaaggag agtactgg                                                   18

<210> SEQ ID NO 31
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 31
tgccggccgg agttcta                                                    17

<210> SEQ ID NO 32
<211> LENGTH: 20
<212> TYPE: DNA
<213> ORGANISM: Artificial Sequence
<220> FEATURE:

<223> OTHER INFORMATION: Synthetic polynucleotide

<400> SEQUENCE: 32
gcccagccaa aactcaggta                                               20

<210> SEQ ID NO 33
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 33
tgaccagttt gatgacgtc                                                19

<210> SEQ ID NO 34
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 34
gtgactccaa tatgcccgaa ga                                            22

<210> SEQ ID NO 35
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 35
tgtttatctg gtgacctttt cagtct                                        26

<210> SEQ ID NO 36
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 36
ccgccaatat gcc                                                      13

<210> SEQ ID NO 37
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 37
tgggatgtcg tggctgtct                                                19

<210> SEQ ID NO 38
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 38
cgtcatcaaa ctggtcagga taat                                          24

<210> SEQ ID NO 39
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 39
cgtgtatcct tctggcacag tgtgc                                           25

<210> SEQ ID NO 40
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 40
gccaccactg tttcatccaa a                                               21

<210> SEQ ID NO 41
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 41
gccgccagtc cttgtcttc                                                  19

<210> SEQ ID NO 42
<211> LENGTH: 18
<212> TYPE: PRT
<213> ORGANISM: Homo sapiens

<400> SEQUENCE: 42

Val Ala Phe Ala Val Val Met Ser Val Gly Met Asp Ser Leu Pro
1               5                   10                  15

Phe Trp

<210> SEQ ID NO 43
<211> LENGTH: 18
<212> TYPE: PRT
<213> ORGANISM: Homo sapiens

<400> SEQUENCE: 43

Pro Gly Ala Leu Thr Asp Tyr Ala Ser Phe Pro Ser Val Leu Ser Ser
1               5                   10                  15

Cys Cys

<210> SEQ ID NO 44
<211> LENGTH: 11
<212> TYPE: PRT
<213> ORGANISM: Homo sapiens

<400> SEQUENCE: 44

Pro Pro Glu Ala Pro Ala Glu Asp Arg Ser Leu
1               5                   10

<210> SEQ ID NO 45
<211> LENGTH: 134
<212> TYPE: PRT
<213> ORGANISM: Homo sapiens

<400> SEQUENCE: 45

```
Ser Pro Asp Lys Gln Met Ala Val Leu Pro Arg Arg Glu Arg Asn Arg
1               5                   10                  15

Gln Ala Ala Ala Ala Asn Pro Glu Asn Ser Arg Gly Lys Gly Arg Arg
            20                  25                  30

Gly Gln Arg Gly Lys Asn Arg Gly Cys Val Leu Thr Ala Ile His Leu
        35                  40                  45

Asn Val Thr Asp Leu Gly Leu Gly Tyr Glu Thr Lys Glu Glu Leu Ile
    50                  55                  60

Phe Arg Tyr Cys Ser Gly Ser Cys Asp Ala Ala Glu Thr Thr Tyr Asp
65                  70                  75                  80

Lys Ile Leu Lys Asn Leu Ser Arg Asn Arg Arg Leu Val Ser Asp Lys
                85                  90                  95

Val Gly Gln Ala Cys Cys Arg Pro Ile Ala Phe Asp Asp Asp Leu Ser
            100                 105                 110

Phe Leu Asp Asp Asn Leu Val Tyr His Ile Leu Arg Lys His Ser Ala
        115                 120                 125

Lys Arg Cys Gly Cys Ile
        130
```

GLIAL CELL LINE-DERIVED NEUROTROPHIC FACTOR (GDNF) COMPOSITIONS AND USE THEREOF

CROSS REFERENCE TO RELATED APPLICATIONS

This application claims the benefit of U.S. Provisional Application No. 61/619,296, filed Apr. 2, 2012, which is herein incorporated by reference in its entirety.

FIELD

This disclosure concerns the identification of primate-specific glial cell line-derived neurotrophic factor opposite strand (GDNFOS) transcripts and peptides, and their use for the treatment of neurodegenerative diseases and diabetes mellitus.

BACKGROUND

Glial cell line-derived neurotrophic factor (GDNF) was initially identified for its ability to promote survival of midbrain dopamine neurons (Lin et al., *Science* 260:1130-1132, 1993) and its neurotrophic actions have been extensively studied in animal models of Parkinson's disease (Chiocco et al., *Parkinsonism Relat Disord* 13 Suppl 3:S321-328, 2007). However, its actions are not specific for dopamine neurons; GDNF regulates neurite branching, synaptic plasticity, and phenotypes of several neuronal populations (Airaksinen and Saarma, *Nat Rev Neurosci* 3:383-394, 2002). Exogenous GDNF supports survival of noradrenergic neurons (Arenas et al., *Neuron* 15:1465-1473, 1995), spinal motor neurons (Henderson et al., *Science* 266:1062-1064, 1994; Trok et al., *Neuroscience* 71:231-241, 1996), peripheral sensory and autonomic neurons (Trupp et al., *J Cell Biol* 130:137-148, 1995), forebrain cholinergic and GABAergic neurons (Williams et al., *J Pharmacol Exp Ther* 277:1140-1151, 1996) and pancreatic β-cells (Mwangi et al., *Gastroenterology* 134:727-737, 2008). Furthermore, GDNF protects the brain from ischemic injury (Wang et al., *J Neurosci* 17:4341-4348, 1997) and ameliorates neuropathic pain (Boucher et al., *Science* 290:124-127, 2000). In peripheral tissues, GDNF promotes differentiation of kidney, lung, pancreas, germ cells, myocytes, and thymocytes, and influences gastrointestinal inflammation and tumorigenesis (Farhi et al., *Fertil Steril* 93:2565-2571, 2010; Kondo et al., *Eur J Immunol* 33:2233-2240, 2003; Little et al., *Curr Top Dev Biol* 90:193-229, 2010; Martinelli et al., *Histochem Cell Biol* 118:337-343, 2002; von Boyen et al., *BMC Gastroenterol* 11:3, 2011; Watanabe et al., *Gastroenterology* 136:2149-2158, 2009; Fromont-Hankard et al., *Arch Pathol Lab Med* 126:432-436, 2002; Lucini et al., *Eur J Histochem* 52:69-74, 2008).

GDNF is synthesized in a precursor form, pre-pro-GDNF, that is processed into the mature form, packaged into vesicles and released upon neuronal activity (Lin et al., *Science* 260: 1130-1132, 1993). Previous studies have shown that the human and rodent GDNF genes have three exons encoding two mRNAs that are produced by alternative splicing of exon 2: pre-(α)long-pro-GDNF and pre-(β)short-pro-GDNF, with the (β)short isoform lacking 26 amino acids in the pro-region (Trupp et al., *J Cell Biol* 130:137-148, 1995; Grimm et al., *Hum Mol Genet.* 7:1873-1886, 1998; Matsushita et al., *Gene* 203:149-157, 1997; Matsushita et al., *Gene* 203:149-157, 1997). Recent studies have indicated that both forms are secreted from neurons, but secretion of the (β)short-pro-GDNF and the corresponding mature GDNF is activity-dependent, whereas (α) long-pro-GDNF and its mature GDNF are secreted constitutively in an adrenal gland pheochromocytoma PC-6.3 cell line (Lonka-Nevalaita et al., *J Neurosci* 30:11403-11413, 2010). Site-directed mutagenesis has shown that the pro-region and C-terminal cysteines are important for GDNF processing and secretion (Oh-hashi et al., *Mol Cell Biochem* 323:1-7, 2009). Pre-pro-GDNF processing and secretion are not well studied with respect to the different isoforms, especially in humans where isoforms are more heterogeneous in pre-pro-regions than in those of the rodent.

GDNF is known to be down-regulated in substantia nigra and putamen in human Parkinson's disease (Backman et al., *Mol Cell Endocrinol* 252:160-166, 2006; Chauhan et al., *J Chem Neuroanat* 21:277-288, 2001; Hunot et al., *J Neural Transm* 103:1043-1052, 1996); however GDNF regulation in Alzheimer's disease (AD) is less documented (Siegel and Chauhan, *Brain Res Brain Res Rev* 33:199-227, 2000). A prior study indicated that GDNF concentrations are significantly up-regulated in cerebrospinal fluid and down-regulated in serum in patients with early AD (Straten et al., *J Alzheimers Dis* 18:331-337, 2009).

SUMMARY

Disclosed herein is the identification of primate-specific glial cell line-derived neurotrophic factor opposite strand (GDNFOS) transcripts and encoded peptides. In particular, disclosed are three GDNFOS antisense transcripts, referred to as GDNFOS-1, GDNFOS-2 and GDNFOS-3, and a 105 amino acid protein encoded by GDNFOS-3.

Provided herein are isolated GDNFOS nucleic acid molecules comprising a nucleotide sequence at least 80% identical to SEQ ID NO: 1 (GDNFOS-1), SEQ ID NO: 2 (GDNFOS-2) or SEQ ID NO: 3 (GDNFOS-3). Also provided are vectors comprising the GDNFOS nucleic acid molecules, isolated host cells comprising such vectors and compositions comprising the GDNFOS nucleic acid molecules.

Further provided are isolated GDNFOS peptides comprising an amino acid sequence at least 80% identical to SEQ ID NO: 4 (GDNFOS-3 protein), or at least 80% identical to a biologically active fragment or variant of GDNFOS-3. In some examples, the GDNFOS-3 fragment comprises SEQ ID NO: 42 (the GFOS3A peptide), SEQ ID NO: 43 (the GFOS3B peptide), or the mature form of GDNFOS-3 (residues 29-105 of SEQ ID NO: 4). Compositions comprising a GDNFOS peptide and a pharmaceutically acceptable carrier are further provided.

Also provided are compositions comprising a GDNFOS nucleic acid molecule and a nucleic acid molecule encoding a GDNF protein, or a biologically active fragment or variant thereof. Similarly, provided by the present disclosure are compositions comprising a GDNFOS peptide and an GDNF protein, or biologically active fragment or variant thereof. In some examples, the GDNF protein is the human mature form of GDNF. In some examples, the biologically active fragment of GDNF comprises the DNSP-11 peptide.

Further provided are methods of treating a neurodegenerative disease or diabetes mellitus in a subject by selecting a subject with a neurodegenerative disease or diabetes mellitus, and administering to the subject a therapeutically effective amount of an isolated GDNFOS nucleic acid, an isolated GDNFOS peptide, or a GDNFOS composition disclosed herein.

Also provided are antibodies that specifically bind a GDNFOS peptide as disclosed herein.

The foregoing and other objects, features, and advantages of the invention will become more apparent from the following detailed description, which proceeds with reference to the accompanying figures.

BRIEF DESCRIPTION OF THE DRAWINGS

FIG. 3 shows GDNFOS-3 nucleotide (SEQ ID NO: 3) and protein (SEQ ID NO: 4) sequences. The nucleotide sequence of the open reading frame (ORF) is represented by bolded upper case letters and non-coding sequence is represented by lower case letters. The nucleotide numbers are marked on the right margin and the amino acid numbers on the left side. The signal peptide and the consensus glycosylation site sequences are underlined and the alternative poly adenylation signals are bold-faced and underlined.

FIG. 7 is an alignment of peptide sequences of human GDNF isoforms (SEQ ID NOs. 5-9). The signal peptide and DNSP-11 peptide are indicated. Boxes indicate protease cleavage sites. Arrow heads denote cysteines that form disulfide bonds and arrows indicate glycosylation sites.

Figure 11A:
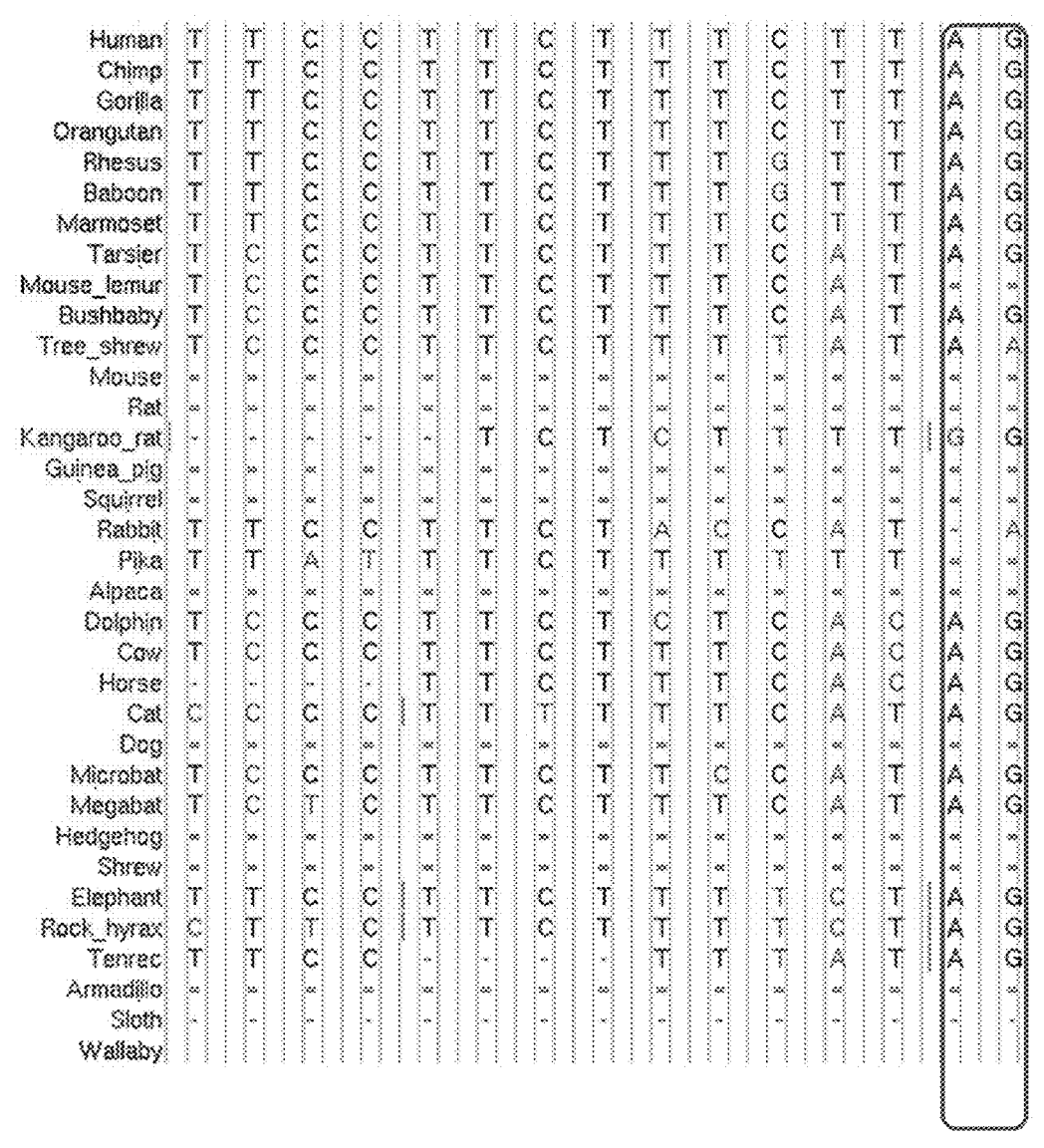
Figure 11C:
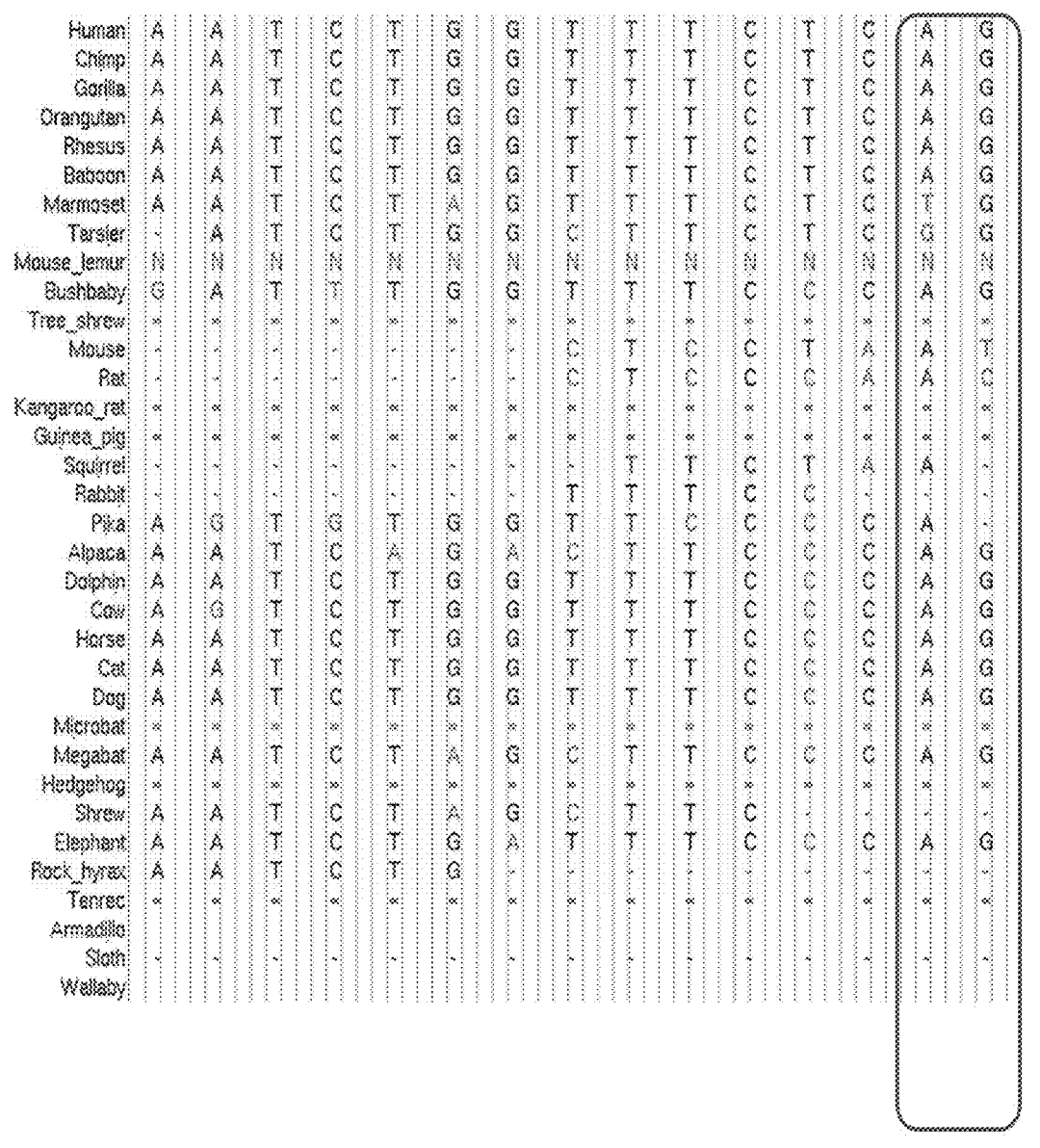

FIGS. 11A-11E show conservation of GDNFOS splicing donor and acceptor sites across mammals. (A) Exon 2 acceptor site of GDNFOS—"AG" is shared across mammals. (B) Exon 2 donor site of GDNFOS—"GT" is shared across mammals. (C) Exon 3 acceptor site of GDNFOS—"AG" is shared across mammals. (D) Exon 3 donor site of GDNFOS—"GT" is shared across mammals. (E) Exon 4 acceptor site of GDNFOS—"AG" is shared across mammals.

SEQUENCE LISTING

Figure 1A:
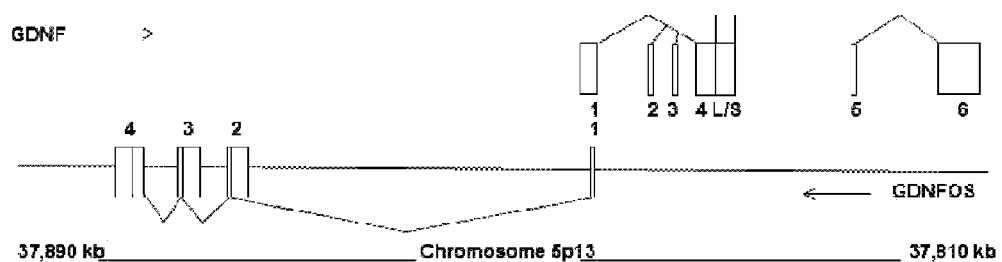
FIG. 1A is a schematic drawing showing the human GDNF/GDNFOS genomic locus, gene structures, and splicing patterns. The boxes represent exons, lines represent introns, and triangles represent splicing patterns.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Feb. 20, 2013, 25.0 KB, which is incorporated by reference herein. In the accompanying sequence listing:

SEQ ID NO: 1 is the nucleotide sequence of GDNFOS-1 (GenBank™ Accession No. JF824130).

SEQ ID NO: 2 is the nucleotide sequence of GDNFOS-2 (GenBank™ Accession No. JF824131).

SEQ ID NO: 3 is the nucleotide sequence of GDNFOS-3 (GenBank™ Accession No. JF824129).

SEQ ID NO: 4 is the amino acid sequence of the GDN-FOS-3 protein.

SEQ ID NO: 5 is the amino acid sequence of human GDNF isoform Ex1_4S.

SEQ ID NO: 6 is the amino acid sequence of human GDNF isoform Ex3_4S.

SEQ ID NO: 7 is the amino acid sequence of human GDNF isoform Ex4S_5.

SEQ ID NO: 8 is the amino acid sequence of human GDNF isoform Ex1_4L.

SEQ ID NO: 9 is the amino acid sequence of human GDNF isoform Ex2_4L.

SEQ ID NO: 10 is the amino acid sequence of a GDNFOS3 C-terminal peptide.

SEQ ID NO: 11 is the amino acid sequence of a GDNF signal peptide.

SEQ ID NOs: 12-41 are nucleotide sequences of PCR primers and probes.

SEQ ID NO: 42 is the amino acid sequence of the GFOS3A peptide.

SEQ ID NO: 43 is the amino acid sequence of the GFOS3B peptide.

SEQ ID NO: 44 is the amino acid sequence of the DNSP-11 peptide.

SEQ ID NO: 45 is the amino acid sequence of the mature form of human GDNF.

DETAILED DESCRIPTION

I. Abbreviations

AD Alzheimer's disease
ALS amyotrophic lateral sclerosis
BBB blood brain barrier
DNSP-11 dopamine neuron stimulating peptide-11
EST expressed sequence tag
GDNF glial cell line-derived neurotrophic factor
GDNFOS glial cell line-derived neurotrophic factor opposite strand
HD Huntington's disease
ICV intracerebroventricular
lncRNA long non-coding RNA
MTG middle temporal gyrus
OFC orbital frontal cortex
ORF open reading frame
PD Parkinson's disease
RT-qPCR reverse transcriptase quantitative polymerase chain reaction
Str striatum
VTA ventral tegmental area II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent (e.g. a nucleic acid molecule or peptide), by any effective route. Exemplary routes of administration include, but are not limited to, injection or infusion (such as subcutaneous, intramuscular, intradermal, intraperitoneal, intrathecal, intravenous, intracerebroventricular, intrastriatal, intracranial and into the spinal cord), oral, intraductal, sublingual, rectal, transdermal, intranasal, vaginal and inhalation routes.

Alzheimer's disease (AD): A progressive brain disorder that occurs gradually and results in memory loss, behavioral and personality changes, and a decline in mental abilities. These losses are related to the death of brain cells and the breakdown of the connections between them. The course of this disease varies from person to person, as does the rate of decline. On average, AD patients live for 8 to 10 years after they are diagnosed, though the disease can last up to 20 years. AD advances by stages, from early, mild forgetfulness to a severe loss of mental function. At first, AD destroys neurons in parts of the brain that control memory, especially in the hippocampus and related structures. As nerve cells in the hippocampus stop functioning properly, short-term memory fails. AD also attacks the cerebral cortex, particularly the areas responsible for language and reasoning.

Amyotrophic lateral sclerosis (ALS): A progressive, usually fatal, neurodegenerative disease caused by the degeneration of motor neurons. As a motor neuron disease, the disorder causes muscle weakness and atrophy throughout the body as both the upper and lower motor neurons degenerate, ceasing to send messages to muscles. Unable to function, the muscles gradually weaken, develop fasciculations (twitches) because of denervation, and eventually atrophy because of that denervation. The patient may ultimately lose the ability to initiate and control all voluntary movement except for the eyes. ALS is also known as Lou Gehrig's disease.

Antibody: A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3rd Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). References to "V_H" or "VH" refer to the variable region of an immunoglobulin heavy chain, including that of an Fv, scFv, dsFv or Fab. References to "V_L" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody.

A "humanized" immunoglobulin is an immunoglobulin including a human framework region and one or more complementarity determining regions (CDRs) from a non-human (for example a mouse, rat, or synthetic) immunoglobulin. The non-human immunoglobulin providing the CDRs is termed a "donor," and the human immunoglobulin providing the framework is termed an "acceptor." Generally, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Biologically active fragment or variant: In the context of the present disclosure, a "biologically active fragment or variant" of a protein, such as a GDNF or GDNFOS protein, is a portion of the protein, or a modified form of the protein, that retains one or more biological activities of the full-length, wild-type protein. For example, biologically active fragments and variants of GDNF include fragments and variants that retain the ability to bind a GDNF receptor (e.g., GFRα1), retain neurotrophic activity, or retain the capacity to increase neuronal survival. In one non-limiting embodiment, the biologically active fragment of GDNF comprises the DNSP-11 peptide (SEQ ID NO: 44). In other non-limiting embodiments, the biologically active fragment of GDNFOS-3 comprises the GFOS3A peptide (SEQ ID NO: 42) or the GFOS3B peptide (SEQ ID NO: 43). In some embodiments, the biologically active fragment of GDNFOS-3 is the mature form of GDNFOS-3 (residues 29-105 of SEQ ID NO: 4), which lack the 28 amino acid signal peptide. One of skill in the art is capable of identifying biologically active variants of GDNF and GDNFOS. In addition, Table 6 provides guidance on conserved sequences in exon 1 of GDNFOS, FIGS. 11A-11E provide guidance on conservation of GDNFOS splice donor and acceptor sites, and Table 4 provides guidance on functional motifs in the GDNFOS-3 protein. Table 5 provides guidance on conserved sequences in exon 2 of GDNF.

Diabetes mellitus: A disease caused by a relative or absolute lack of insulin leading to uncontrolled carbohydrate metabolism. Type 1 diabetes (sometimes referred to as "insulin-dependent diabetes" or "juvenile-onset diabetes") is an auto-immune disease characterized by destruction of the pancreatic β cells that leads to a total or near total lack of insulin. In type 2 diabetes (T2DM; sometimes referred to as "non-insulin-dependent diabetes" or "adult-onset diabetes"), the body does not respond to insulin, though it is present. Symptoms of diabetes include: excessive thirst (polydipsia); frequent urination (polyuria); extreme hunger or constant eating (polyphagia); unexplained weight loss; presence of glucose in the urine (glycosuria); tiredness or fatigue; changes in vision; numbness or tingling in the extremities (hands, feet); slow-healing wounds or sores; and abnormally high frequency of infection. Diabetes may be clinically diagnosed by a fasting plasma glucose (FPG) concentration of greater than or equal to 7.0 mmol/L (126 mg/dL), or a plasma glucose concentration of greater than or equal to 11.1 mmol/L (200 mg/dL) at about two hours after an oral glucose tolerance test (OGTT) with a 75 g load. A more detailed description of diabetes may be found in *Cecil Textbook of Medicine*, J. B. Wyngaarden, et al., eds. (W.B. Saunders Co., Philadelphia, 1992, 19$^{th}$ ed.).

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain to internal stop codons. For example, a fusion protein can include GDNFOS peptide fused to a heterologous protein.

Glial cell line-derived neurotrophic factor (GDNF): A highly conserved and potent neurotrophic factor. The recombinant form of GDNF protein has been shown to promote the survival and differentiation of dopaminergic neurons in vitro and in vivo. Subsequent studies indicated that GDNF plays a role in neuritic outgrowth or survival of mesencephalic dopaminergic neurons, cranial and spinal cord motor neurons, brainstem noradrenergic neurons, basal forebrain cholinergic neurons, Purkinje cells, and specific groups of dorsal ganglia and sympathetic neurons (Connor and Dragunow, *Brain Res Brain Res Rev* 27:1-39, 1998; Lapchak et al., *Cell Tissue Res* 286:179-189, 1996; Levy et al., *Biodrugs* 19(2): 97-127, 2005). The GDNF protein is processed to a mature secreted form that exists as a homodimer. The mature form of the protein is a ligand for the product of the RET (rearranged during transfection) proto-oncogene. Multiple transcript variants encoding different isoforms have been found for the GDNF gene. GDNF nucleic acid and protein sequences from a variety of different species are publically available, such as through GenBank™. In particular, human GDNF sequences can be found under NCBI Gene ID 2668. An exemplary sequence for the mature form of human GDNF is set forth herein as SEQ ID NO: 45.

Glial cell line-derived neurotrophic factor opposite strand (GDNFOS): A gene transcribed by the opposite (antisense) strand of the GDNF gene. As used herein, "GDNFOS" also refers to the transcripts and proteins encoded by the GDN-FOS gene. The GDNFOS gene includes four exons that are spliced into three different isoforms (see FIGS. 1A and 1B). GDNFOS-1 and GDNFOS-2 are long non-coding RNAs (lncRNAs) and GDNFOS-3 encodes a protein of 105 amino acids, which contains a 28 amino acid signal peptide.

Huntington's disease (HD): A neurodegenerative genetic disorder that affects muscle coordination and leads to cognitive decline and psychiatric problems. The disease is caused by an autosomal dominant mutation in the Huntingtin gene. Expansion of a CAG triplet stretch within the Huntingtin gene results in a mutant form of the huntingtin protein, which gradually damages cells in the brain. Physical symptoms of the disease can begin at any age, but typically arise between ages 35 and 44. The earliest symptoms are often subtle problems with mood or cognition. A general lack of coordination and an unsteady gait often follows. As the disease progresses, uncoordinated, jerky body movements become more apparent, along with a decline in mental abilities and behavioral and psychiatric problems. Physical abilities are gradually impeded until coordinated movement becomes very difficult. Mental abilities generally decline into dementia.

Isolated: An "isolated" biological component (such as a nucleic acid molecule, protein, or cell) has been substantially separated or purified away from other biological components in the cell, blood or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Multiple sclerosis (MS): A slowly progressive CNS disease characterized by disseminated patches of demyelination in the brain and spinal cord, resulting in multiple and varied neurological symptoms and signs, usually with remissions and exacerbation. The symptoms of MS include weakness, lack of coordination, paresthesias, speech disturbances, and visual disturbances, most commonly double vision. More specific signs and symptoms depend on the location of the lesions and the severity and destructiveness of the inflammatory and sclerotic processes. Relapsing-remitting multiple sclerosis is a clinical course of MS that is characterized by clearly defined, acute attacks with full or partial recovery and no disease progression between attacks. Secondary-progressive multiple sclerosis is a clinical course of MS that initially is relapsing-remitting, and then becomes progressive at a variable rate, possibly with an occasional relapse and minor remission. Primary progressive multiple sclerosis presents initially in the progressive form. A clinically isolated syndrome is the first neurologic episode, which is caused by inflammation/demyelination at one or more sites in the CNS.

Neurodegenerative disorder or disease: Refers to any type of disorder or disease that is associated with a progressive loss of motor, sensory and/or perceptual functions, and often involves behavioral and cognitive deficits. Neurodegenerative diseases are typically characterized by the progressive loss of structure or function of neurons, such as neurons within the cerebral cortex, basal ganglia, cerebellum, brain stem or motor systems. Neurodegenerative disorders include, but are not limited to, Alzheimer's disease, Parkinson's disease, Huntington's disease, ALS, multiple sclerosis, Lewy body dementia, vascular dementia, progressive supranuclear palsy, corticobasal degeneration, multiple system atrophy and frontotemporal dementia.

ORF (open reading frame): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Parkinson's disease (PD): A degenerative disorder of the central nervous system that impairs motor skills, cognitive processes, and other functions. Parkinson's disease is also referred to as Parkinson disease, Parkinson's, PD and primary parkinsonism. The most obvious symptoms of Parkinson's disease are motor-related, including tremor, rigidity, slowness of movement and postural instability. Among non-motor symptoms are autonomic dysfunction and sensory and sleep difficulties. Cognitive and neurobehavioral problems, including dementia, are common in the advanced stages of the disease.

In subjects that develop Parkinson's disease, symptoms typically begin around the age of 60, although there are young-onset cases. Symptoms result from insufficient formation and action of dopamine produced in the dopaminergic neurons of the midbrain (specifically the substantia nigra). Pathologically the disease is characterized by the accumulation of alpha-synuclein protein forming inclusions called Lewy bodies. Such pathology can only be demonstrated at autopsy so diagnosis is mainly clinical (based on symptoms). Some tests such as neuroimaging techniques can also aid in diagnosis.

Peptide or Polypeptide: A polymer in which the monomers are amino acid residues which are joined together through amide bonds. When the amino acids are alpha-amino acids, either the L-optical isomer or the D-optical isomer can be used, the L-isomers being preferred. The terms "peptide," "polypeptide" or "protein" as used herein are intended to encompass any amino acid sequence and include modified sequences such as glycoproteins. The terms "peptide" and "polypeptide" are specifically intended to cover naturally occurring proteins, as well as those which are recombinantly or synthetically produced.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences that directs transcription of a nucleic acid. A promoter includes necessary nucleic acid sequences near the start site of transcription. A promoter also optionally includes distal enhancer or repressor elements which can be located as much as several thousand base pairs from the start site of transcription. Both constitutive and inducible promoters are included (see e.g., Bitter et al., *Methods in Enzymology* 153: 516-544, 1987).

Recombinant: A recombinant nucleic acid molecule or peptide is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Sequence identity/similarity: The identity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Subject: Living multi-cellular vertebrate organisms, a category that includes both human and veterinary subjects, including human and non-human mammals (including research subjects such as rodents). A subject is also referred to herein as a "patient."

Therapeutically effective amount: A quantity of a specified composition, pharmaceutical or therapeutic agent (such as a nucleic acid molecule or peptide) sufficient to achieve a desired effect in a subject, or in a cell, being treated with the agent. The effective amount of the agent will be dependent on several factors, including, but not limited to the subject being treated, the disease or condition being treated, and the manner of administration of the therapeutic composition. In some embodiments of the present disclosure, the therapeutically effective amount (or effective amount) of a GDNFOS nucleic acid or peptide is an amount sufficient to ameliorate one or more signs or symptoms of a neurodegenerative disease, delay the progression of the disease, and/or prolong survival of the subject with the disease.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is a plasmid vector. In other embodiments, the vector is a viral vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. All GenBank™ Accession numbers are incorporated herein by reference as they appear in the database on Mar. 15, 2012. In case of conflict, the present specification, including explanations of terms, will control. In addition, the materials, methods, and examples are illustrative only and not intended to be limiting.

III. Overview of Several Embodiments

Figure 4A:
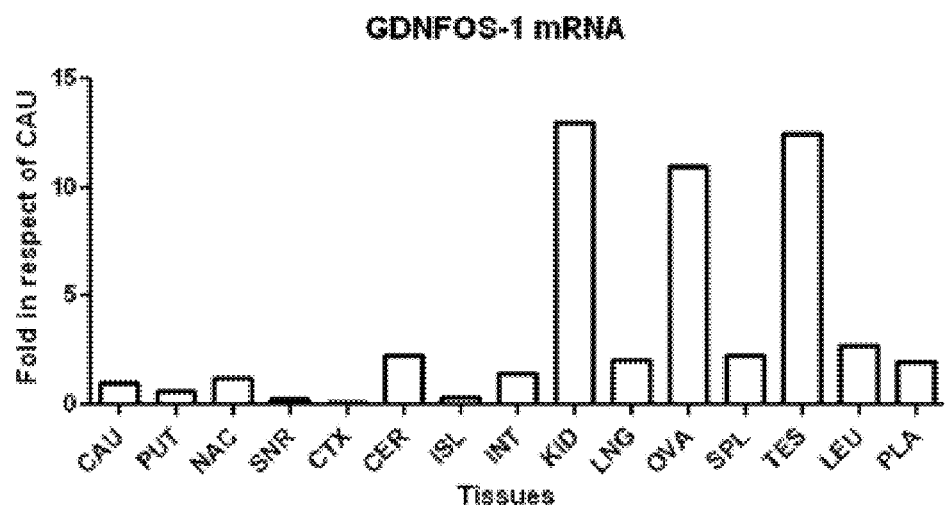
FIG. 4A is a graph showing GDNFOS-1 mRNA levels in human brain regions and peripheral tissue. CAU=caudate; PUT=putaman; NAC=nucleus accumbens; SNR=substantia nigra; CTX=cortex; CER=cerebellum; ISL=pancreatic islets; INT=intestine; KID=kidney; LNG=lung; OVA=ovary; SPL=spleen; TES=testis; LEU=leukocytes; and PLA=placenta.
Figure 4B:
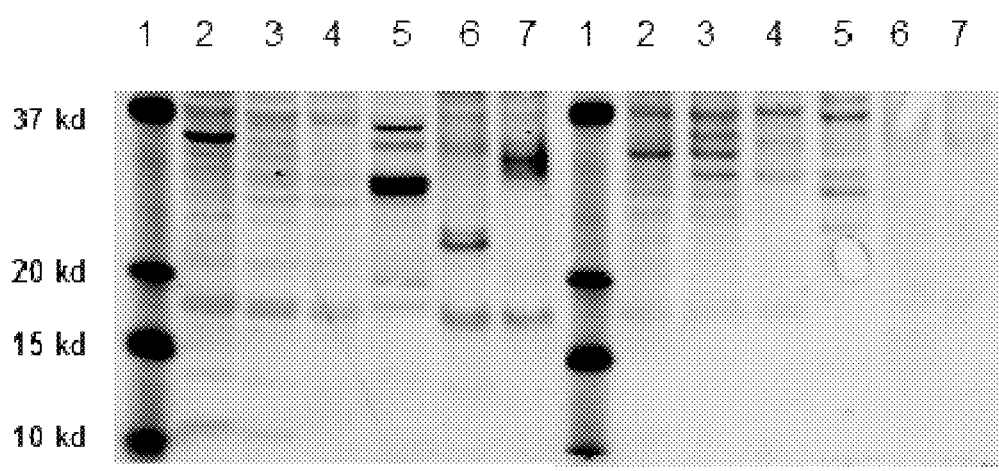
FIG. 4B is an immunoblot showing GDNFOS-3 protein levels in human, hamster, and rat cell lines and tissues. Lane assignments are as follows: 1—molecular weight marker; 2—HEK293 cells; 3—SH-SY5Y cells; 4—CHO cells; 5—human middle temporal gyrus (MTG); 6—rat kidney; and 7—rat prefrontal cortex. The gel on the right shows immunostaining with GDNFOS-3 antibody and the gel on the left shows the results of pre-absorption with GDNFOS-3 antigenic peptide before incubation with the primary antibody.

Disclosed herein is the identification of a gene transcribed from the opposite (antisense) strand of the GDNF gene, referred to as GDNFOS. One of the three alternatively spliced GDNFOS isoforms (GDNFOS-3) encodes a peptide of 105 amino acids (see FIGS. 1A and 1B), which is expressed in human cell lines and tissues (FIG. 4B).

Provided herein are isolated GDNFOS nucleic acid molecules. In some embodiments, the GDNFOS nucleic acid molecules comprise a nucleotide sequence at least 80%, at least 85%, at least 90%, at least 95%, at least 96%, at least 97%, at least 98% or at least 99% identical to SEQ ID NO: 1 (GDNFOS-1), SEQ ID NO: 2 (GDNFOS-2) or SEQ ID NO: 3 (GDNFOS-3). In particular examples, the nucleotide sequence of the GDNFOS nucleic acid molecule comprises or consists of SEQ ID NO: 1, SEQ ID NO: 2 or SEQ ID NO: 3.

Also provided are isolated GDNFOS peptides encoded by the GDNFOS nucleic acid molecules disclosed herein. In some examples, the amino acid sequence of the GDNFOS peptide comprises SEQ ID NO: 4, or a biologically active fragment or variant thereof. In particular non-limiting examples, the biologically active fragment of GDNFOS comprises the amino acid sequence of SEQ ID NO: 42 (the GFOS3A peptide) or SEQ ID NO: 43 (the GFOS3B peptide). In some examples, the biologically active fragment of GDNFOS is the mature form of the GDNFOS-3 protein (residues 29-105 of SEQ ID NO: 4).

Further provided are vectors comprising the GDNFOS nucleic acid molecules disclosed herein. In some embodiments, the vector is a plasmid vector. In other embodiments, the vector is a viral vector. Viral vectors can be, for example, adenovirus, adeno-associated virus, retrovirus (such as lentivirus), herpes virus or vaccinia virus vectors. Viral vectors can include modified versions of the viruses, such as replication deficient viruses. Suitable vectors, such as gene therapy vectors, are well known in the art.

Also provided are isolated cells comprising a GDNFOS nucleic acid molecule disclosed herein, and isolated cells comprising a vector that includes a GDNFOS nucleic acid molecule.

Further provided herein are compositions comprising a GDNFOS nucleic acid molecule or vector as disclosed herein. In some embodiments, the compositions further include a pharmaceutically acceptable carrier. In some embodiments, the compositions further comprise a nucleic acid molecule encoding a glial cell line-derived neurotrophic factor (GDNF) protein, or a biologically active fragment or variant thereof. In some examples, the GDNF protein comprises human GDNF of SEQ ID NO: 45. In one non-limiting example, the biologically active fragment of GDNF comprises the DNSP-11 peptide of SEQ ID NO: 44, which for example may be used synergistically with GDNF and GDNFOS-3 peptides in treatments for neurodegenerative disease and diabetes mellitus.

Further provided are isolated GDNFOS peptides comprising an amino acid sequence at least 80%, at least 85%, at least 90%, at least 95%, at least 96%, at least 97%, at least 98% or at least 99% identical to SEQ ID NO: 4 (GDNFOS-3), SEQ ID NO: 42 (the GFOS3A peptide), SEQ ID NO: 43 (the GFOS3B peptide) or residues 29-105 of SEQ ID NO: 4 (mature GDNFOS-3). The GFOS3A peptide is an 18 amino acid peptide corresponding to residues 29-46 of GDNFOS-3 (SEQ ID NO: 4), which is the portion of the GDNFOS-3 protein between the signal peptide and the consensus glycosylation site (see FIG. 3). The GFOS3B peptide is an 18 amino acid peptide corresponding to residues 75-92 of the GDNFOS-3 protein (SEQ ID NO: 4). In some embodiments, the amino acid sequence of the GDNFOS peptide comprises or consists of SEQ ID NO: 4, SEQ ID NO: 42, SEQ ID NO: 43 or residues 29-105 of SEQ ID NO: 4.

Also provided are fusion proteins comprising GDNFOS, or a fragment or variant thereof, fused to a heterologous protein. In some examples, the heterologous protein is a reporter molecule, such as a fluorescent protein or enzyme. In other examples, the heterologous protein is a protein tag (for example an affinity tag), such as a His tag, FLAG tag, myc tag, chitin binding protein (CBP), maltose binding protein (MBP) or glutathione-S-transferase (GST). In yet other examples, the heterologous protein is a carrier protein, such as keyhole limpet hemocyanin (KLH), bovine serum albumin (BSA) or ovalbumin (OVA).

Further provided are compositions comprising the GDNFOS peptides, or GDNFOS fusion proteins, and a pharmaceutically acceptable carrier. In some embodiments, the compositions further comprise a GDNF protein, or a biologically active fragment or variant thereof. In some examples, the GDNF protein comprises human GDNF of SEQ ID NO: 45. In some examples, the biologically active fragment of GDNF comprises the DNSP-11 peptide of SEQ ID NO: 44.

In the context of the present disclosure, GDNF or GDNFOS protein variants include GDNF or GDNFOS proteins having at least one amino acid substitution, deletion or addition relative to the wild-type protein. In some instances, the amino acid substitution(s) is a conservative substitution. In some examples, deletion variants include proteins with deletions of about 1-5 amino acids, about 1-10 amino acids, or about 1-20 amino acids. Deletions include N-terminal, C-terminal and internal deletions. GDNF or GDNFOS fragments include, for example, fragments of at least 10, at least 20, at least 30, at least 40, at least 50, at least 60, at least 70 or at least 80 amino acids. Biologically active fragments and variants of GDNF or GDNFOS are variants and fragments that retain at least one activity of the native protein, such as neurotrophic activity. Methods of making protein fragments and variants are well known in the art. Exemplary GDNF variants and fragments are described in U.S. Patent Application Publication No. 2003/0050273. Exemplary GDNFOS fragments are provided herein as SEQ ID NO: 42 and SEQ ID NO: 43. In some examples, the GDNFOS fragment is the mature form of GDNFOS-3 (lacking the 28 amino acid signal peptide), corresponding to residues 29-105 of SEQ ID NO: 4. One of skill in the art is capable of identifying biologically active variants of GDNF and GDNFOS. In addition, Table 6 provides guidance on conserved sequences in exon 1 GDNFOS, FIGS. 11A-11E provide guidance on conservation of splice acceptor and donor sites in GDNFOS and Table 4 provides guidance on functional motifs of the GDNFOS-3 protein. Table 5 provides guidance on conserved sequences in exon 2 of GDNF.

Also provided herein are methods of treating a neurodegenerative disease or diabetes mellitus in a subject by selecting a subject with a neurodegenerative disease or diabetes mellitus, and administering to the subject a therapeutically effective amount of an isolated GDNFOS nucleic acid molecule, a vector comprising a GDNFOS nucleic acid molecule, a GDNFOS composition, or an isolated GDNFOS peptide as disclosed herein.

In some embodiments, the neurodegenerative disease is selected from Alzheimer's disease, Parkinson's disease, Huntington's disease, multiple sclerosis and amyotrophic lateral sclerosis. In some embodiments, the diabetes mellitus is diabetes mellitus type 1.

The mode of administration of the GDNFOS composition (including GDNFOS nucleic acid molecules, vectors, peptides and pharmaceutical compositions) will vary depending upon, for example, the particular composition being administered, the disease being treated and the desired therapeutic outcome. One of skill in the art is capable of selecting an appropriate composition and route of administration based on the therapeutic goal. Exemplary routes and methods of administration are discussed further in section IV below.

Further provided herein are antibodies, or antigen-binding fragments thereof, that specifically bind an epitope of a GDNFOS peptide. In some embodiments, the antibody or antigen-binding fragment thereof specifically binds an epitope of human GDNFOS of SEQ ID NO: 4.

In some embodiments, the antibody is a polyclonal antibody. In other embodiments, the antibody is a monoclonal antibody. In some embodiments, the antibodies are mouse, rat or rabbit antibodies.

In some embodiments, the antigen-binding fragment is an Fab, Fab', F(ab)'$_2$ scFv or dsFv. In other embodiments, the antibodies are humanized antibodies or fully human antibodies. In other embodiments, the antibodies are chimeric antibodies.

Methods of generating monoclonal and polyclonal antibodies are well known in the art and are described in section V below.

IV. Administration of GDNFOS Compositions

Provided herein are methods of treating neurodegenerative diseases and diabetes mellitus by administering a GDNFOS peptide or nucleic acid molecule (such as a vector comprising a GDNFOS nucleic acid molecule), or compositions comprising the peptides or nucleic acid molecules. The route of administration of the GDNFOS composition will vary depending on, for example, the particular composition being administered, the disease being treated and the intended target site for delivery of the GDNFOS peptide or nucleic acid molecule. Methods of administering therapeutic proteins and nucleic acid molecules are well known in the art and appropriate modes of administration can be determined by a skilled practitioner depending upon the desired therapeutic outcome. Exemplary methods of administering GDNFOS peptides and nucleic acid molecules are discussed below.

Nucleic acid molecules and peptides can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Administration can be accomplished by single or multiple doses. The dose required will vary from subject to subject depending on the species, age, weight and general condition of the subject, the particular nucleic acid molecule or peptide being used and its mode of administration. An appropriate dose can be determined by one of ordinary skill in the art using only routine experimentation.

A. Administration of GDNFOS and GDNF Nucleic Acid Molecules

Methods of administering nucleic acid molecules to a subject are well known in the art and include, for example, delivery of naked DNA molecules (such as by gene gun), administration in combination with a delivery reagent (such as a liposome), or by using a recombinant plasmid or viral vector.

In some embodiments of the present disclosure, GDNFOS and/or GDNF nucleic acid molecules are administered to a subject using liposomes, which can increase the blood half-life of nucleic acids. Suitable liposomes for use with the present disclosure can be formed from standard vesicle-forming lipids, which generally include neutral or negatively charged phospholipids and a sterol, such as cholesterol. The selection of lipids is generally guided by consideration of several factors, such as the desired liposome size and half-life of the liposomes in the blood stream. A variety of methods are known in the art for preparing liposomes (see, for example, Szoka et al., *Ann. Rev. Biophys. Bioeng.* 9:467, 1980; and U.S. Pat. Nos. 4,235,871; 4,501,728; 4,837,028; and 5,019,369).

In some embodiments, polymers can be used to deliver a nucleic acid molecule to a subject. Cationic lipids and polymers that can be used to deliver therapeutic nucleic acid molecules have been described (see, for example, Zhang et al., *J Control Release.* 123(1):1-10, 2007; Vorhies et al., *Methods Mol Biol.* 480:11-29, 2009; and U.S. Patent Application Publication No. 2009/0306194). Polypeptide carriers can also be used to administer nucleic acid molecules to a subject (see, for example, Rahbek et al., *J. Gene Med.* 10:81-93, 2008).

In other embodiments herein, the GDNFOS and/or GDNF nucleic acid molecules are delivered using a viral vector. A number of different viral vector systems have been used for the delivery of neurotrophic factors, including lentivirus vectors, adenovirus vectors and adeno-associated virus (AAV) vectors (Levy et al., *Biodrugs* 19(2):97-127, 2005; Davidson and Breakefield, *Nat Rev Neurosci* 4:353-353-364, 2003; US Patent Application Publication Nos. 2003/0050273 and 2004/0202642).

For example, recombinant virus vectors containing GDNFOS and/or GDNF nucleic acid molecules can be introduced into cells of the CNS using either in vivo or ex vivo transduction techniques to treat a neurodegenerative disease. For transduction ex vivo, the desired recipient cell can be removed from the subject, transduced with viral vector (or recombinant virus particles) and reintroduced into the subject. Alternatively, syngeneic or xenogeneic cells can be used where those cells will not generate an inappropriate immune response in the subject. Additionally, neural progenitor cells can be transduced ex vivo and then delivered to the CNS (US Patent Application Publication No. 2003/0050273).

For in vivo delivery, viral vector (or cells transduced ex vivo) can be delivered directly to the CNS or brain by injection into, for example, the ventricular region, the striatum (e.g., the caudate nucleus or putamen of the striatum), the spinal cord, or substantia nigra. In some cases, administration is carried out using a needle, catheter or related device, using neurosurgical techniques known in the art, such as by stereotactic injection (see, e.g., Stein et al., *J Virol* 73:3424-3429, 1999; Davidson et al., *Proc Natl Acad Sci USA* 97:3428-3432, 2000; Davidson et al., *Nat Genet.* 3:219-223, 1993; and Alisky and Davidson, *Hum Gene Ther* 11:2315-2329, 2000).

In some embodiments, the viral vector, such as a lentiviral vector, is administered to a peripheral site. In some examples, the viral vector is administered intramuscularly. The viral vector can reach distant target sites via the neurons that innervate the muscle (US Patent Application Publication No. 2004/0202642).

Administration to the CNS can also be achieved using the convection-enhanced delivery (CED) system. Using CED, recombinant virus vectors can be delivered to many cells over large areas of the brain. Moreover, the delivered vectors efficiently express transgenes in CNS cells (e.g., neurons or glial cells). Any convection-enhanced delivery device is appropriate for delivery of viral vectors. In some examples, the device is an osmotic pump or an infusion pump. Both osmotic and infusion pumps are commercially available from a variety of suppliers. Typically, a viral vector is delivered via CED devices by inserting a catheter, cannula or other injection device into CNS tissue in the subject in need of treatment. One of skill in the art could readily determine which general area of the CNS is an appropriate target depending on the disease to be treated. For example, to treat PD, the striatum is a suitable area of the brain to target. CED delivery is described in, for example, U.S. Pat. No. 6,309,634.

In some embodiments, administration of the GDNFOS and/or GDNF nucleic acid molecule is used for the treatment of diabetes mellitus. It has previously been shown that GDNF enhances survival of pancreatic islet cells (U.S. Patent Application Publication No. 2008/0187522; Mwangi et al., *Transplantation* 92(7):745-751, 2011). Accordingly, the present disclosure contemplates the administration and delivery of GDNFOS alone or in combination with GDNF to pancreatic islet cells. In some embodiments, viral vectors are used to mediate delivery of GDNFOS and/or GDNF to pancreatic islet cells.

B. Administration of GDNFOS and GDNF Peptides

Methods of administering therapeutic proteins and peptides are well known in the art. In some embodiments of the disclosed methods, GDNFOS and/or GDNF peptides are administered to a subject for the treatment of a neurodegenerative disease or diabetes mellitus. When administering GDNFOS and/or GDNF peptide, one must consider the appropriate target site based on the disease to be treated. If the site of action is the central nervous system, the protein must be able to cross the blood brain barrier (BBB) or be delivered directly to the target site in the brain.

Methods of administering neurotrophic factors for the treatment of a variety of neurodegenerative diseases has been previously described (see, for example, Levy et al., *Biodrugs* 19(2):97-127, 2005; Gill et al., *Nat Med* 9:589-595, 2003; Nutt et al., *Neurology* 60:69-73, 2003; Olson et al., *J Neural Transm Park Dis Dement Sect* 4:79-95, 1992; Eriksdotter et al., *Dement Geriatr Cogn Disord* 9:246-257, 1998; Bradley, *Ann Neurol* 38:971, 1995; The BDNF Study Group Phase III, *Neurology* 52:1427-1433, 1999; Ochs et al., *Amyotroph Lateral Scler Other Motor Neuron Disord* 1:201-206, 2000; ALS CNTF Treatment Study Group, *Neurology* 46(5):1244-1249, 1996; Miller et al., *Neurology* 47:1329-1331, 1996; Miller et al., *Ann Neurol* 39:256-260, 1996; Lai et al., *Neurology* 49:1621-1630, 1997; Borasio et al., *Neurology* 51:583-586, 1998).

In some embodiments, the GDNFOS and/or GDNF peptide is administered by direct infusion into the brain, such as by intracerebroventricular (ICV) injection, intrastriatal injection, intranigral injection, intracerebral injection, or infusion into the putamen. In particular examples, the neurodegenerative disease to be treated is Parkinson's disease (PD) and the GDNFOS and/or GDNF peptide is administered by continuous infusion into the cerebral ventricles or into the putamen (such as by using a catheter) or by bolus ICV injections. In other examples, PD is treated by intrastriatal or intranigral injection.

In some examples, the neurodegenerative disease to be treated is Alzheimer's disease and the GDNFOS and/or GDNF peptide is administered by ICV infusion.

In some examples, the neurodegenerative disease to be treated is ALS and the GDNFOS and/or GDNF peptide is administered by intrathecal infusion (such as by using an implanted pump) or by subcutaneous injection.

Intranasal administration of peptides also leads to delivery to the CNS. Thus, in some examples, the GDNFOS and/or GDNF peptide is administered intranasally in the treatment of a neurodegenerative disease.

In some embodiments, GDNFOS and/or GDNF peptides are administered using biodegradable microparticles (~1-100 μm) or nanoparticles (~50-1000 nm). Nanoparticles and microparticles (also known as nanospheres are microspheres) are drug delivery vehicles that can carry encapsulated drugs such as synthetic small molecules, proteins, peptides, cells and nucleic acid based biotherapeutics for either rapid or controlled release. A variety of molecules (e.g., proteins, peptides and nucleic acid molecules) can be efficiently encapsulated in nano/microparticles using processes well known in the art.

The nano/microparticles for use with the methods described herein can be any type of biocompatible particle, such as biodegradable particles, such as polymeric particles, including, but not limited to polyamide, polycarbonate, polyalkene, polyvinyl ethers, and cellulose ether nano/microparticles. In some embodiments, the particles are made of biocompatible and biodegradable materials. In some embodiments, the particles include, but are not limited to particles comprising poly(lactic acid) or poly(glycolic acid), or both poly(lactic acid) and poly(glycolic acid). In particular embodiments, the particles are poly(D,L-lactic-co-glycolic acid) (PLGA) particles.

Other biodegradable polymeric materials are contemplated for use with the methods described herein, such as poly(lactic acid) (PLA) and polyglycolide (PGA). Additional useful nano/microparticles include biodegradable poly(alkylcyanoacrylate) particles (Vauthier et al., *Adv. Drug Del. Rev.* 55:519-48, 2003).

Various types of biodegradable and biocompatible nano/microparticles, methods of making such particles, including PLGA particles, and methods of encapsulating a variety of synthetic compounds, proteins and nucleic acids, has been well described in the art (see, for example, U.S. Publication No. 2007/0148074; U.S. Publication No. 20070092575; U.S. Patent Publication No. 2006/0246139; U.S. Pat. No. 5,753,234; U.S. Pat. No. 7,081,489; and PCT Publication No. WO/2006/052285).

Microspheres containing neurotrophic factors have been shown to release bioactive neurotrophic factors for at least 2 months in the brain following intrastriatal administration in rats (Jollivet et al., *Neurosci Lett* 356:207-210, 2004). In addition, microsphere-mediated delivery of growth factor proteins to the central and peripheral nervous system has been described in, for example, US Patent Application Publication No. 2011/0217264.

V. GDNFOS Antibodies

Provided by the present disclosure are antibodies or antibody fragments that specifically bind an epitope of a GDN- FOS peptide, such as an epitope of human GDNFOS of SEQ ID NO: 4. In some embodiments, provided are polyclonal antibodies specific for a GDNFOS peptide. In other embodiments, provided are monoclonal antibodies specific for a GDNFOS peptide.

Methods of making polyclonal and monoclonal antibodies are well known, and are described below. Polyclonal antibodies, antibodies which consist essentially of pooled monoclonal antibodies with different epitopic specificities, as well as distinct monoclonal antibody preparations, are contemplated. The preparation of polyclonal antibodies is well known to those skilled in the art (see, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992). For example, an antigen (such as a GDNFOS peptide) is administered to a host animal such as, but not limited to, a rabbit, mouse or rat, to induce the production of antisera containing polyclonal antibodies specific for the antigen. Various adjuvants can be used to increase the immunological response, depending on the host species. Exemplary adjuvants include Freund's (complete and incomplete) adjuvant, mineral gels such as aluminum hydroxide, surface active substances such as lysolecithin, pluronic polyols, polyanions, peptides, oil emulsions, keyhole limpet hemocyanins and dinitrophenol. Such adjuvants are well known in the art.

The preparation of monoclonal antibodies likewise is conventional (see, for example, Kohler & Milstein, *Nature* 256: 495, 1975; Coligan et al., sections 2.5.1-2.6.7; and Harlow et al. in:*Antibodies: a Laboratory Manual*, page 726, Cold Spring Harbor Pub., 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, e.g., Coligan et al., sections 2.7.1-2.7.12 and sections 2.9.1-2.9.3; Barnes et al., Purification of Immunoglobulin G (IgG), in: *Methods in Molecular Biology*, Vol. 10, pages 79-104, Humana Press, 1992).

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, such as syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from a subhuman primate antibody. General techniques for raising therapeutically useful antibodies in baboons can be found, for example, in PCT Publication No. WO 91/11465; and Losman et al., *Int. J. Cancer* 46:310, 1990.

Alternatively, an antibody that specifically binds a GDNFOS peptide can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Natl. Acad. Sci. U.S.A.* 86:3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993.

Antibodies can also be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433, 1994. Cloning and expression vectors that are useful for producing a human immunoglobulin phage library can be obtained, for example, from Stratagene Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994.

Antibodies include intact molecules as well as fragments thereof, such as Fab, F(ab')$_2$, and Fv which are capable of binding the epitopic determinant. These antibody fragments retain some ability to selectively bind with their antigen and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody, defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York, 1988).

Antibodies can be prepared using an intact polypeptide or fragments containing small peptides of interest as the immunizing antigen. The polypeptide or a peptide used to immunize an animal can be derived from substantially purified polypeptide produced in host cells, in vitro translated cDNA, or chemical synthesis which can be conjugated to a carrier protein, if desired. Such commonly used carriers which are chemically coupled to the peptide include keyhole limpet hemocyanin, thyroglobulin, bovine serum albumin, and tetanus toxoid. The coupled peptide is then used to immunize the animal (e.g., a mouse, a rat, or a rabbit).

Monoclonal antibodies can also be prepared by well-known recombinant methods or using phage display. In some embodiments, monoclonal antibodies are generated using any phage display method known in the art. In phage display methods, functional antibody domains are displayed on the surface of phage particles which carry the polynucleotide sequences encoding them. In some cases, the phage displays antigen binding fragments, such as Fab and Fv or disulfide-bond stabilized Fv, expressed from a repertoire or combinatorial antibody library (e.g., human or murine). Phage expressing an antigen binding fragment is generally selected using labeled antigen or antigen bound or captured to a solid surface or bead. Phages used in these methods are typically filamentous phage, such as M13 phage. Generally, the antigen binding fragments are expressed as a recombinantly fused protein to either the phage gene III or gene VIII protein. Exemplary phage display methods are described in Brinkman et al. (*J Immunol Methods* 182:41-50, 1995), Ames et al. (*J Immunol Methods* 184:177-186, 1995), Kettleborough et al. (*Eur J Immunol* 24:952-958, 1994), Persic et al. (*Gene* 187: 9-18, 1997), Burton et al. (*Advances in Immunology*, 57:191-280, 1994), and in PCT Publication Nos. WO 90/02809; WO 91/10737; WO 92/01047; WO 92/18619; WO 93/11236; WO 95/15982; WO 95/20401; and in U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

After phage selection, the antibody coding regions from the phage are isolated and can be used to generate whole antibodies, including human antibodies, or any other desired fragments, and expressed in any desired host, including mammalian cells, insect cells, plant cells, yeast, and bacteria.

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (see, for example, Coligan et al., Unit 9, *Current Protocols in Immunology*, Wiley Interscience, 1991).

The following examples are provided to illustrate certain particular features and/or embodiments. These examples should not be construed to limit the disclosure to the particular features or embodiments described.

EXAMPLES

Example 1

Materials and Methods

This example describes the experimental procedures for the studies described in Example 2.

Bioinformatic Analysis of GDNF and GDNFOS Isoforms

It was determined that the human GDNF gene contains more spliced ESTs in the UCSC genome browser than the rat gene. The human expressed sequence tag (EST) database was searched to identify additional human GDNF exons. Human exons 1, 4 and 6 were found to be homologous to rat exons 1, 2 and 3, respectively. Using Sequencher software (Gene Code Corporation, Ann Arbor, Mich.), additional human exons 2, 3 and 5 were identified that are aligned to the EST clones and human GDNF genomic sequence. Human GDNF isoform nucleotide sequences were translated into amino acid sequences using the ExPASy™ translation tool and the peptide sequences were aligned using CLUSTALW software.

In addition, a natural antisense gene (GDNFOS: GDNF Opposite Strand) transcribed from the antisense strand of GDNF gene was also found by EST sequence alignments and Sanger sequencing (Eurofins, Huntsville, Ala.) of three IMAGE human cDNA clones. The pre-pro-GDNF domains and potential modification sites were identified by InterProScan. Based on the possible isoform differences between rat and human, evolutionary analysis of the splicing junctions was carried out in UCSC syntenic genomic alignment using BLASTZ followed by chaining and netting pipeline (Kent et al., *Proc. Natl. Acad. Sci. USA* 100:11484-11489, 2003; Schwartz et al., Genome Res 13:103-107, 2003; Blanchette et al., *Genome Res.* 14:708-715, 2004). The protein domains of potential open reading frames of GDNFOS-3 were analyzed by ExPaSy™ proteomic tools.

Human Postmortem Brain Samples and Rat Tissues

Post mortem middle temporal gyrus (MTG) samples of controls (CON), AD and HD subjects were obtained; the diagnoses of the subjects were all confirmed by autopsy (Troncoso et al., *Ann Neurol* 43:673-676, 1998). The RNA integrity of each sample was analyzed by the Agilent RNA 6000 Nano kit with Bioanalyzer (Agilent Technologies, Santa Clara, Calif.). Human brain and peripheral tissue cDNAs were synthesized using pooled total RNA purchased from Clontech (Palo Alto, Calif.). Human pancreatic islets were obtained from the Integrated Islet Distribution Program (IIDP, NIDDK, NIH). Male Sprague Dawley rats (300-400 g, Charles River, Raleigh, N.C.) were sacrificed by decapitation and the brains were rapidly frozen in −50° C. isopentane solution and stored at −80° C. freezer. Tissue punches of the brain regions were taken from 1 mm coronal sections cut in a cryostat at −20° C. The peripheral tissues were dissected on ice and immediately frozen by dry ice.

Quantitative RT-PCR Analysis of GDNF Isoforms

Total RNAs were isolated using the TRIZOL Reagent and single strand cDNAs were synthesized using the Superscript III first strand cDNA synthesis kit according to the manufacturer's protocols (Invitrogen, Life Technologies, Carlsbad, Calif.). TaqMan™ probes (FIG. 1 and Table 1) were designed using Primer Express 3.0 (Applied Biosystems, Life Technologies, Carlsbad, Calif.) at the splicing junctions of the different human and rat GDNF and GDNFOS isoforms for RT-qPCR analysis. The rat endogenous control was Fam-labeled Ube2i (Table 1, synthesized by Integrated DNA Technologies, Inc. Coralville, Iowa.). The human endogenous control was Fam-labeled β-actin (Applied Biosystems). The RT-qPCR assays were carried out with Advanced TaqMan™ Fast Universal PCR Master Mix in a 7500 Fast TaqMan™ instrument (Applied Biosystems, Life Technologies, Carlsbad, Calif.) using a default thermo-cycling program. Technical duplicates and triplicates were carried out in the qPCR assays. Pooled human tissue samples were used for the tissue expression assay. Twenty human AD, 8 HD and 19 control middle temporal gyrus samples, respectively, were assayed to compare expression of human GDNF and GDNFOS isoforms. Ct (cycle threshold) values of more than 36 represented very low mRNA levels and were therefore deleted from the analysis. Mann-Whitney u tests of Prizm software (GraphPad Software, La Jolla, Calif.) was used to analyze RT-qPCR.

TABLE 1

TaqMan ™ MGB probe and primer sequences

| Isoform | Probe or Primer | Sequence | SEQ ID NO: |
|---|---|---|---|
| hEx1_4 | Probe | ATCCGAGGTGCCGCC | 12 |
|  | Forward primer | CACCTGGAGTTAATGTCCAACCT | 13 |
|  | Reverse primer | CGACATCCCATAACTTCATCTTAAAG | 14 |
| hEx2_4 | Probe | AAAACTTTCAAGACAAATGCAGT | 15 |
|  | Forward primer | TTCGGGTATACCACGGAGGAT | 16 |
|  | Reverse primer | CGGCACCATTGCTGTTAGG | 17 |
| hEx3_4 | Probe | CAGGCTGGGTGCCG | 18 |
|  | Forward primer | TGCTCTCGCAACAGAATACCTATT | 19 |
|  | Reverse primer | CGACATCCCATAACTTCATCTTAAAG | 20 |
| hEx5_6 | Probe | ATGTAGCCGAGACATT | 21 |
|  | Forward primer | GGCACAGGAAGATGACTTGATG | 22 |
|  | Reverse primer | TCCTCTGGCATATTTGCTCTTG | 23 |
| hGDNF-αL | Probe | TCCTGATCAGTTCGATGAT | 24 |
|  | Forward primer | AGTGACTCAAATATGCCAGAGGATT | 25 |
|  | Reverse primer | TCAGTCTTTTAATGGTGGCTTGAA | 26 |
| hGDNF-βS | Probe | ATTATCCTGATCAGTTCGATG | 27 |
|  | Forward primer | CCCGCCGCAAATATGC | 28 |
|  | Reverse primer | TCAGTCTTTTAATGGTGGCTTGAA | 29 |
| hGDNFOS-1 | Probe | CGAGAAGGAGAGTACTGG | 30 |
|  | Forward primer | TGCCGGCCGGAGTTCTA | 31 |
|  | Reverse primer | GCCCAGCCAAAACTCAGGTA | 32 |
| rGDNF-αL | Probe | TGACCAGTTTGATGACGTC | 33 |
|  | Forward primer | GTGACTCCAATATGCCCGAAGA | 34 |
|  | Reverse primer | TGTTTATCTGGTGACCTTTTCAGTCT | 35 |
| rGDNF-βS | Probe | CCGCCAATATGCC | 36 |
|  | Forward primer | TGGGATGTCGTGGCTGTCT | 37 |

TABLE 1-continued

TaqMan ™ MGB probe and primer sequences

| Isoform | Probe or Primer | Sequence | SEQ ID NO: |
|---|---|---|---|
|  | Reverse primer | CGTCATCAAACTGGTCAGGATAAT | 38 |
| rUbe2i | Probe | CGTGTATCCTTCTGGCACAGTGTGC | 39 |
|  | Forward primer | GCCACCACTGTTTCATCCAAA | 40 |
|  | Reverse primer | GCCGCCAGTCCTTGTCTTC | 41 |

Western Blot Analysis of GDNF and GDNFOS

A polyclonal goat antibody for GDNF (AF-2,2-NA, R&D Systems, Minneapolis, Minn.) was used for Western blot to detect GDNF mature peptide as described previously (Airavaara et al., *Addict Biol* 16(2):261-272, 2011). An affinity purified anti-GDNFOS antibody was developed by injecting rabbit with epitope peptide (CKGMSHGQHFTHT; SEQ ID NO: 10) located at the C-terminus (Genemed Synthesis, Inc. San Antonio, Tex.). The antibody was used for Western blot of HEK293, SH-SY5Y, and CHO cell lines and tissues of human and rat. Student's t-test was used to analyze Western blot data.

Example 2

Identification of Novel GDNF Isoforms and a Cis-Antisense GDNFOS Gene

This example describes the identification of novel isoforms of GDNF and a cis-natural antisense transcript, and their regulation in the human middle temporal gyrus of patients with Alzheimer's disease.

The Human GDNF Gene has Six Exons and Multiple Isoforms

A search of the human dbEST followed by RT-qPCR analysis identified six exons in the human GDNF gene (FIG. 1A). A comparison with the rat GDNF gene structure revealed that three exons, human GDNF exons 1, 4 short, 4 long, and 6 are conserved with rat GDNF exons 1, 2 short, 2 long, and 3, respectively. The human GDNF exons 2, 3, and 5 sequences are aligned (FIG. 1) with human EST clones AJ001897, AJ001899 and DQ235474, respectively. The original translation initiation methionine of GDNF is located in human exon 4. InterProScan indicated that the GDNF isoform with exon 2 (Ex2_4) contains another initiation codon that translates into a 35 amino acid signal peptide, in contrast to GDNF isoforms with exons 1 or 3 (Ex1_4 and Ex3_4, respectively), which each contain an 18 amino acid signal peptide. The insertion of human exon 5 between exon 4 short and 6 creates a truncated GDNF isoform (Ex5_6) which potentially utilizes the downstream initiation methionine encoded by exon 6. The truncated GDNF isoform Ex5_6 contains only 20 amino acids of the pro-region before the furin endoproteinase cleavage site and InterProScan indicated that the 20 amino acid sequence is not a signal peptide. Therefore, human GDNF isoforms of Ex1_4L, Ex1_4S, Ex3_4S, Ex2_4L, and Ex4S_5 encode 211, 185, 185, 228, and 159 amino acids, respectively, and the peptide sequence differences among the isoforms are located in the pre-pro-regions of GDNF. All of the human GDNF isoforms encode the identical mature GDNF peptide (FIG. 7).

Human GDNF isoform expression patterns in brain regions and peripheral tissues were investigated using isoform-specific TaqMan™-MGB probes (FIG. 1 and Table 1). Human caudate pre-(β)short-proGDNF isoform (Ex4S6) mRNA was used as a reference. The human pre-(α)long-proGDNF isoform (Ex4L6) mRNA levels were highest in striatum, intestine, and kidney while the pre-(β)short-proGDNF isoform (Ex4S6) mRNA levels were highest in intestine and kidney (Table 2).

RT-qPCR showed that human GDNF exon 1 (Ex1_4) transcript level is highest in brain and peripheral tissues except for pancreatic islets where exon 2 (Ex2_4) transcript is higher. The exon 3 (Ex3_4) transcript was not found in most tissues except for low levels in intestine and kidney. The exon 5 (Ex5_6) transcript was either not detected or was at very low levels in putaman, nucleus accumbens, cortex, hypothalamus, and intestine (Table 2). The ratios of the human GDNF α-long and β-short isoforms were higher in brain regions and pancreatic islets than the ratios of α-long and β-short in peripheral tissues (Table 2).

TABLE 2

Human GDNF isoform expression using hGDNF-βS in caudate as a reference

| Isoform | CAU | PUT | NAC | SNR | CTX | AMG | HIP | HTH | ISL | INT | KID | MUS |
|---|---|---|---|---|---|---|---|---|---|---|---|---|
| Ex1_4 | 4.56 | 5.47 | 2.36 | 1.97 | 1.49 | 0.99 | 1.39 | 2.19 | 8.04 | 17.88 | 17.01 | 0.54 |
| Ex2_4* | 0.47 | 0.28 | 0.94 | 0.45 | 0.50 | 0.06 | 0.11 | 0.12 | 12.35 | 0.63 | 0.77 | 0 |
| Ex3_4* | 0 | 0 | 0 | 0 | 0 | 0 | 0 | 0 | 0 | 0.24 | 0.56 | 0 |
| Ex5_6* | 0 | 0.39 | 0.26 | 0 | 0.29 | 0.35 | 0 | 0.40 | 0 | 0.52 | 0 | 0 |
| hGDNF-αL | 50.63 | 35.35 | 19.17 | 21.72 | 10.82 | 3.67 | 7.33 | 4.89 | 86.56 | 40.47 | 30.41 | 0.15 |
| hGDNF-βS | 1 | 1.47 | 0.76 | 0.51 | 0.56 | 0.49 | 0.41 | 0.50 | 1.06 | 7.29 | 4.31 | 0.11 |
| Ratio α:β | 50.6 | 24.1 | 25.2 | 42.6 | 19.3 | 7.5 | 17.9 | 9.8 | 81.7 | 5.6 | 7.1 | 1.4 |

*= Primate-specific forms

Comparison of Rat GDNF Isoform mRNA and Protein Tissue Expression

Using specific TaqMan™ probes for rat pre-(α)long-proGDNF and pre-(β)short-proGDNF isoforms (Table 1) and, for reference the pre-(β)short-proGDNF isoform (rGDNFβS) in rat dorsal striatum, it was determined that mRNA for pre-(α)long-proGDNF isoform (rGDNFαL) was expressed several fold higher than that of the pre-(β)short-proGDNF isoform (rGDNFβS) across brain regions and peripheral tissues. The highest mRNA expressions were in dorsal striatum and nucleus accumbens, and ovary, lung, and stomach and lower levels in prefrontal cortex and amygdala (Table 3). The human α-long and β-short ratios were several fold higher than rat α-long and β-short ratios (Tables 2 and 3). As the long pre-(α)long-proGDNF isoform contains the dopamine neuron stimulating peptide-11 (DNSP-11) (Bradley et al., *PLoS One* 5:e9752, 2010; Immonen et al., *Exp Neurol* 210:793-796, 2008), this 11 mer peptide encoded transcript is expressed at higher level in human than rat brain.

TABLE 3

Rat GDNF isoform expression (n = 3) using rGDNF-βS in dorsal striatum as a reference

| Isoform | DST | NAC | PFC | AMG | STM | TES | LNG | OVA | SPL |
|---|---|---|---|---|---|---|---|---|---|
| rGDNF-αL | 4.67 ± 0.46 | 2.63 ± 0.24 | 0.66 ± 0.05 | 0.82 ± 0.16 | 1.31 ± 0.01 | 0.47 ± 0.22 | 2.25 ± 0.12 | 2.97 ± 0.55 | 0.29 ± 0.05 |
| rGDNF-βS | 1.00 ± 0.09 | 0.65 ± 0.05 | 0.11 ± 0.01 | 0.17 ± 0.04 | 0.29 ± 0.04 | 0.19 ± 0.11 | 0.38 ± 0.03 | 0.56 ± 0.06 | 0.05 ± 0.01 |
| Ratio α:β | 4.7 ± 0.39 | 4.0 ± 0.11 | 6.0 ± 0.67 | 4.8 ± 0.52 | 4.5 ± 0.69 | 2.5 ± 0.77 | 5.9 ± 0.23 | 5.3 ± 0.41 | 5.8 ± 0.60 |

Figure 2A:
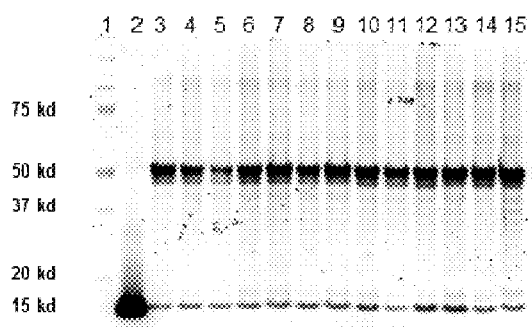
FIG. 2A is an immunoblot showing rat mature GDNF protein expression in several brain regions. Lane assignments are as follows: 1—precision molecular weight marker; 2—recombinant GDNF under reducing conditions; 3—medial prefrontal cortex; 4—dorsal prefrontal cortex; 5—ventral prefrontal; 6—temporal cortex; 7—nucleus accumbens; 8—dorsal striatum; 9—hippocampus CA1; 10—hippocampus CA2&3; 11—hippocampus dentate gyrus; 12—amygdala; 13—thalamus; 14—hypothalamus; and 15—cerebellum.
Figure 2B:
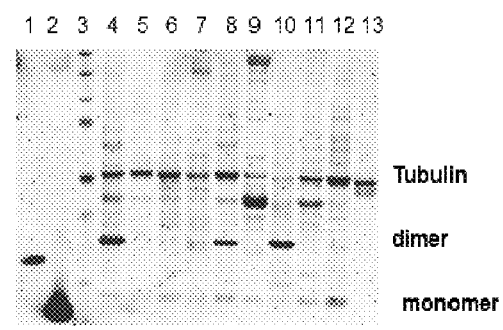
FIG. 2B is an immunoblot showing rat mature GDNF protein expression in several different tissues. Lane assignments are as follows: 1—recombinant GDNF under non-reducing conditions; 2—recombinant GDNF under reducing conditions; 3—precision molecular weight marker; 4—heart; 5—intestine; 6—kidney; 7—liver; 8—lung; 9—muscle; 10—spleen; 11—stomach; 12—testis; and 13—spinal cord.

CAU, caudate;
PUT, putaman;
NAC, nucleus accumbens;
DST, dorsal striatum;
SNR, substantia nigra;
PFC, prefrontal cortex;
AMG, amygdala;
HIP, hippocampus;
HTH, hypothalamus;
ISL, pancreatic islets;
INT, intestine;
KID, kidney;
MUS, muscle;
STM, stomach;
TES, testis;
OVA, ovary;
SPL, spleen Western blot analysis was used to detect both GDNF monomers and dimers using a goat polyclonal antibody (Airavaara et al., Addict Biol 16(2):261-272, 2011). Relatively even levels of mature GDNF monomers were found in various brain regions and low monomer levels were found in peripheral tissues, except for higher levels of GDNF dimers in heart, lung and spleen (FIGS. 2A and 2B). The differences between dimers and monomers of GDNF in different tissues might represent differential posttranslational modification such as disulfide bonds and glycosylation of the mature GDNF peptides in rat brain regions and peripheral tissues (indicated by arrow heads at cysteine and arrows to asparagine in FIG. 7). Western blot analysis showed that GDNF peptide levels did not correlate with mRNA levels in brain regions where the striatal levels were several times higher than that of pre-frontal cortex. The discordance between GDNF mRNA and the mature peptide in different brain regions could be due to cell type specific expression of GDNF isoforms and transportation of mature peptide along neuronal processes (Wang et al., J Neurosci 30:14502-14512, 2010).

GDNFOS is Transcribed from the Opposite Strand of the GDNF Gene

Figure 1B:
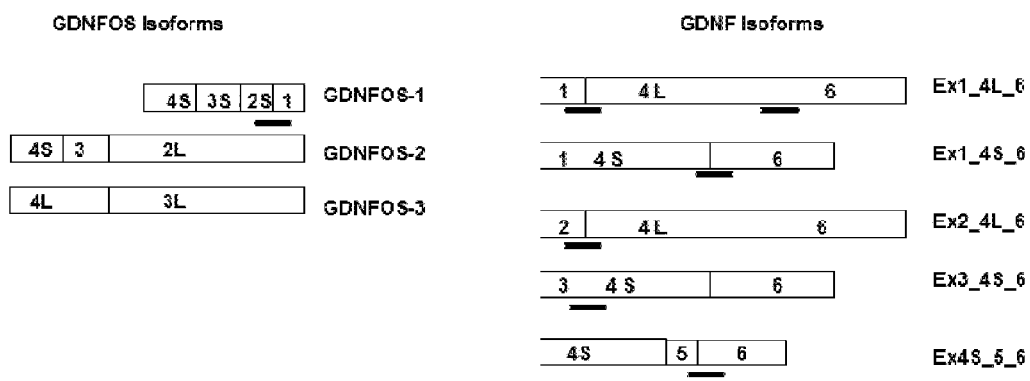
FIG. 1B is a schematic drawing showing transcripts of GDNF and GDNFOS isoforms and TaqMan™ probe designs. Boxes represent spliced exons and the TaqMan™ probes are marked between exon junctions.

By searching the human dbEST database followed by RT-qPCR analysis and sequencing of the IMAGE cDNA clones, a cis-natural antisense transcript (GDNFOS) gene was identified from the opposite strand of GDNF (FIG. 1A). The GDNFOS gene contains 4 exons and three initiation sites for transcription, i.e. exon 1, exon 2-long and exon 3-long for GDNFOS-1, -2 and -3, respectively (FIG. 1B).

The first exon of the GDNFOS-1 isoform has 136 nucleotides reverse complementarity (head-to-head configuration) (Zhang et al., Nucleic Acids Res 34:3465-3475, 2006) to the 5'UTR of the GDNF isoform Ex1_4 (FIG. 1A). The exon 1 of the GDNFOS-1 isoform is spliced to the exon 2-short, exon 3-short (intra-exonal splicing events) and exon 4-short (alternative poly adenylation event). The exon 2-long of GDNFOS-2 isoform is spliced to the exon 3-short and exon 4-short. The exon3-long of GDNFOS-3 isoform is spliced to exon 4-long (alternative poly adenylation event, FIG. 1B). The GDNFOS-2 and GDNFOS-3 transcripts do not overlap with the GDNF sense transcripts. IMAGE clones of 277201, 1762317, and 1637129 were sequenced in two directions to obtain the sequences of GDNFOS-1, -2, and -3 (GenBank™ accession numbers: JF824130 (SEQ ID NO: 1), JF824131 (SEQ ID NO: 2), and JF824129 (SEQ ID NO: 3), respectively).

GDNFOS-1 and -2 IMAGE clones contain the upstream poly A site to produce 618 bp and 2,944 bp transcripts, respectively. GDNFOS-1 and -2 are predicted long-non-coding RNAs (lncRNAs) (Lipovich et al., Biochim Biophys Acta 1799:597-615, 2010), with no open reading frame (ORF) of more than 60 amino acids. The GDNFOS-3 IMAGE clone contains the downstream alternative adenylation site to produce a 1,963 bp transcript that potentially encodes an ORF of 105 amino acids (FIG. 3). The calculated molecular weight and isoelectric point of the ORF are 11.86 kDa and pI=8.47, respectively. The proteome and pathway analysis found that the ORF contains an N-terminal 28 amino acid signal peptide, an internal ASN-glycosylation site, two cysteines, an endoplasmic reticulum (ER) targeting sequence (Predotar) in a secreted pathway (Secretome 2.0 server). There is a single furin-type cleavage site after the signal peptide between the residue 28-29 and the mature peptide contains interface amino acids of Pro, Ile, Tyr, Trp and Arg involved in protein-protein interactions (Sillerud and Larson, Curr Protein Pept Sci 6:151-169, 2005).

As noted above, the GDNFOS-3 protein is 105 amino acids in length (set forth herein as SEQ ID NO: 4). Using the Eukaryotic Linear Motif (ELM) resource, several functional motifs were identified in GDNFOS-3 (see Table 4 below). All amino acid positions listed in Table 4 are in reference to SEQ ID NO: 4.

TABLE 4

Functional Motifs of GDNFO-3 Protein

| Motif Name | Positions | Description |
| --- | --- | --- |
| LIG_CYCLIN_1 | 54-58 | Substrate recognition site that interacts with cyclin and thereby increases phosphorylation by cyclin/cdk complexes; also used by cyclin inhibitors. |
| LIG_PDZ_3 | 47-50 | Class III PDZ domains binding motif |
| LIG_SH3_3 | 55-61 | Motif recognized by those SH3 domains with a non-canonical class I recognition specificity |
| MOD_CK1_1 | 69-75 83-89 86-92 | CK1 phosphorylation site |
| MOD_GSK3_1 | 76-83 83-90 | GSK3 phosphorylation recognition site |
| MOD_N-GLC_1 | 46-51 | Generic motif for N-glycosylation |
| TRG_ENDOCYTIC_2 | 81-84 | Tyrosine-based sorting signal responsible for the interaction with mu subunit of adaptor protein (AP) complex |

Human Tissue Expression of GDNFOS

The exon-intron junctions of human GDNFOS are conserved at splicing donor (GT) and acceptor (AG) sites and the first large intron (31,778 bp) is followed by small introns of 959 and 436 bp for intron 2 and 3, respectively. A TaqMan™ probe (FIG. 1B and Table 1) was designed at the splicing junction of GDNFOS gene exons 1 and 2 to investigate the tissue expression patterns of the GDNFOS-1 transcript. The highest mRNA levels of GDNFOS-1 were found in kidney, ovary, and testis where GDNFOS-1 mRNA is more than 10-fold of that of brain caudate region; higher expression was also observed in cerebellum and nucleus accumbens relative to other brain areas (FIG. 4A). The transcriptional level of GDNFOS-1 is lower than that of GDNF isoform Ex1_4 in all brain regions.

The affinity purified antibody against the C-terminal peptide (CKGMSHGQHFTHT; SEQ ID NO: 10) of GDNFOS3 recognized an 11 kDa band in Western blot of human embryonic kidney (HEK293) and neuroblastoma (SH-SY5Y) cell lines but not in the Chinese hamster ovary (CHO) cell line (FIG. 4B). A 22 kDa band was also observed in human MTG but not in rat kidney (FIG. 4B, left); however, rat prefrontal cortex showed a 30 kDa signal that could be blocked by the immunogenic peptide. The 11 kDa and 22 kDa bands could be completely blocked by pre-incubation of the antibody with the antigenic peptide (FIG. 4B, right). The 11 kDa and 22 kDa may represent GDNFOS mature peptide monomer and dimer, respectively. The 30 kDa band might be a structural homologue of rat brain because the exon 4 of GDNFOS is shared in rat genome.

Accelerated Primate Evolution of GDNF/GDNFOS Locus

The finding of human GDNF and GDNFOS isoforms may indicate that the locus is a primate accelerated region (Dorus et al., Cell 119:1027-1040, 2004). Comparative genomics of the mVISTA and UCSC genome browser of the 46-way vertebrate alignments (Rhead et al., Nucleic Acids Res 38:D613-619, 2010) was used to examine the conservation and the distribution of the splicing structure of GDNF and GDNFOS in different species and the ORF of GDNF on the vertebrate phylogenetic tree. The GDNF/GDNFOS locus predates the vertebrate split, i.e., it is largely shared across fish and humans but absent in invertebrates.

Insertions, deletions or stop codons were manually removed in non-human species and this codon-based alignment was fed into CODEML (Yang, *Mol. Biol. Evol.* 24:1586-1591, 2007). As a result, it was found that exon 2 of human GDNF is only shared by primates and some rodents given the narrow distribution of the exon donor sequence GT in these species. The species other than primates either do not contain the translation initiation codon (ATG) or lost their exon donor sequence (Table 5). InterProScan predicted that GDNF exon 2 encodes an extended and primate-specific signal peptide (MQSLPNSNGAAAGRDFK; SEQ ID NO: 11) in frame with exon 4. Potentially primate-specific GDNF exon 3 appears to be shared by multiple mammalian groups given the existence of GT in outgroups, suggesting it is an ancestral form. The splicing junctions (AG/GT) of GDNF exon 5 appear constrained in primate but divergent in other placental mammals. However, the exon 3 and 5 sequences were not found in EST databases of other species except for that of human.

which demonstrates that GDNFOS is a hominoid young gene with coding potential (Yang, *Mol. Biol. Evol.* 24:1586-1591, 2007).

TABLE 6

GDNFOS exon 1 alignment of multiple species
(splicing donor sites are in bold)

| Human | G | A | A | G | G | A | G | A | G | G | T |
|---|---|---|---|---|---|---|---|---|---|---|---|
| Chimp | G | A | A | G | G | A | G | A | G | G | T |
| Gorilla | G | A | A | G | G | A | G | A | G | G | T |
| Orangutan | G | A | A | G | G | A | G | A | G | G | T |
| Rhesus | G | A | A | G | G | A | G | A | G | A | T |
| Baboon | G | A | A | G | G | A | G | A | G | A | T |
| Marmoset | G | A | A | G | A | A | G | A | G | G | T |
| Mouse lemur | G | A | A | G | G | A | G | A | G | A | T |
| Bushbaby | G | — | A | G | G | A | G | A | G | A | T |
| Tree shrew | G | G | A | G | G | A | G | C | G | A | T |
| Mouse | G | A | A | G | A | A | G | A | A | G | C |
| Rat | — | A | A | G | A | A | G | A | A | G | C |
| Kangaroo rat | A | A | A | G | G | A | G | A | G | A | T |
| Guinea pig | G | A | A | G | G | A | A | A | G | A | T |
| Squirrel | G | G | A | G | G | A | G | A | G | A | T |
| Rabbit | G | G | G | G | G | A | G | A | G | A | C |

TABLE 5

GDNF exon 2 alignment of multiple species in reverse orientation

| Human | G | A | A | A | T | G | G | N | S | N | P | L | S | Q | M |
|---|---|---|---|---|---|---|---|---|---|---|---|---|---|---|---|
| Chimp | G | A | A | A | T | G | G | N | S | N | P | L | S | Q | M |
| Gorilla | G | A | A | G | T | G | G | N | S | N | P | L | S | Q | M |
| Orangutan | G | A | A | A | T | G | G | N | S | N | P | L | S | Q | M |
| Rhesus | G | A | A | A | T | G | G | N | S | N | P | L | S | Q | M |
| Baboon | G | A | A | A | T | G | G | N | S | N | P | L | S | Q | M |
| Marmoset | G | A | A | A | T | G | G | N | S | N | P | L | S | Q | I |
| Mouse lemur | G | A | A | A | T | G | G | N | S | N | P | L | S | Q | T |
| Bushbaby | G | A | A | A | T | G | G | K | S | N | P | L | S | Q | M |
| Tree shrew | G | A | A | A | T | G | G | N | S | N | P | L | S | Q | A |
| Mouse | A | A | A | A | T | G | G | S | N | T | P | P | S | Q | I |
| Rat | A | A | A | A | T | G | G | H | S | T | P | L | S | R | I |
| Kangaroo rat | A | A | A | G | G | G | G | H | G | P | P | S | P | Q | G |
| Guinea pig | — | — | A | C | G | G | C | C | K | P | P | L | P | L | L |
| Rabbit | N | N | N | N | N | N | N | N | N | N | N | N | N | N | N |
| Pika | A | T | A | — | — | — | — | — | — | —TG | P | L | A | * | C |
| Alpaca | G | A | A | A | T | C | S | D | S | N | P | L | S | Q | M |
| Dolphin | G | A | A | A | T | C | G | N | S | N | P | L | S | Q | R |
| Cow | G | A | A | A | T | C | G | N | C | N | P | L | S | Q | R |
| Horse | G | A | A | A | T | C | S | N | S | D | P | L | S | Q | L |
| Cat | G | G | G | G | T | C | G | N | S | N | P | — | — | Q | M |
| Dog | — | — | A | A | T | C | G | H | I | AA— | — | — | — | Q | M |
| Microbat | N | N | N | N | N | N | N | N | N | N | N | N | N | N | N |
| Megabat | G | A | A | A | T | C | G | K | S | N | P | L | S | Q | M |
| Shrew | G | G | A | A | G | G | G | G | R | S | P | L | S | R | M |
| Elephant | G | A | A | A | T | T | G | N | S | N | P | L | S | R | M |
| Rock hyrax | G | A | A | A | T | T | G | K | S | N | P | L | S | Q | I |
| Tenrec | G | A | C | C | C | A | R | N | S | D | P | L | S | P | L |
| Armadillo | G | A | A | A | T | G | G | N | S | N | P | F | S | Q | M |

Amino acids (in bold) are represented as a single letter code, and splicing donor sites (GT) are underlined. "N" represents sequences that are unavailable. Together with the start codon information, the new open reading frame introduced by exon 2 is primate-specific.

The GDNFOS exon 1 may be unique in hominoids (human and apes) given the occurrence of the AT-GT substitutions in the splicing donor site in monkey and other mammalian genomes (Table 6). Although GDNFOS exon 2, 3 and 4 splicing acceptor and donor sites are shared across mammals, a TG-AG mutation was observed in the splicing acceptor site of GDNFOS exon 3 in the marmoset genome (FIGS. 11A-11E). Since the GDNFOS was found in humans, it should be expected that the evolutionary branch towards human demonstrates a different ratio of non-synonymous substitution rate and synonymous substitution rate (Ka/Ks) compared to other branches. The Ka/Ks value in human branch is 0.9, A genome alignment of the locus encoding the 105 amino acid GDNFOS-3 peptide across 46 vertebrate species indicates that the locus is shared across mammals but absent in other vertebrates. The existence of numerous gaps in the alignment suggests that the orthologous loci in some mammals may be not able to encode this ORF. A sequence alignment of the first 60 base pairs of the GDNFOS-3 ORF indicates that this ORF is not at all conserved. The start codon is disabled in opossum, dog, mouse and orangutan. For example, there are small base pair (1-2 bp) insertions and deletions in the mouse sequence which will cause frameshifts. Based on the sequence alignments, only humans, chimpanzees and rhesus macaques are likely to encode this ORF.

Figure 5A:
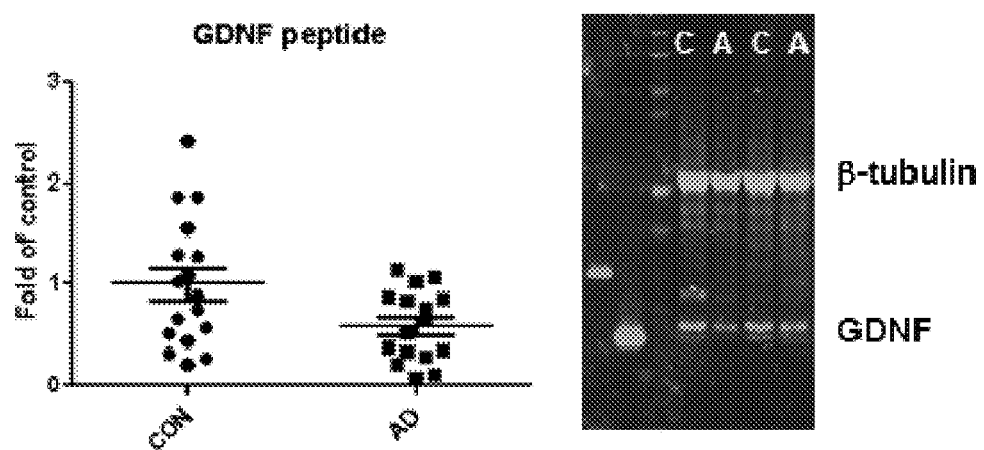
FIG. 5A shows expression of GDNF mature peptide in Alzheimer's disease (AD) subjects. Shown on the left is a scatter plot of AD MTG normalized by control. The Y axis is the fold change over control. The Western blot on the right shows GDNF mature peptide levels in MTG of control (C) and AD (A) subjects.
Figure 5B:
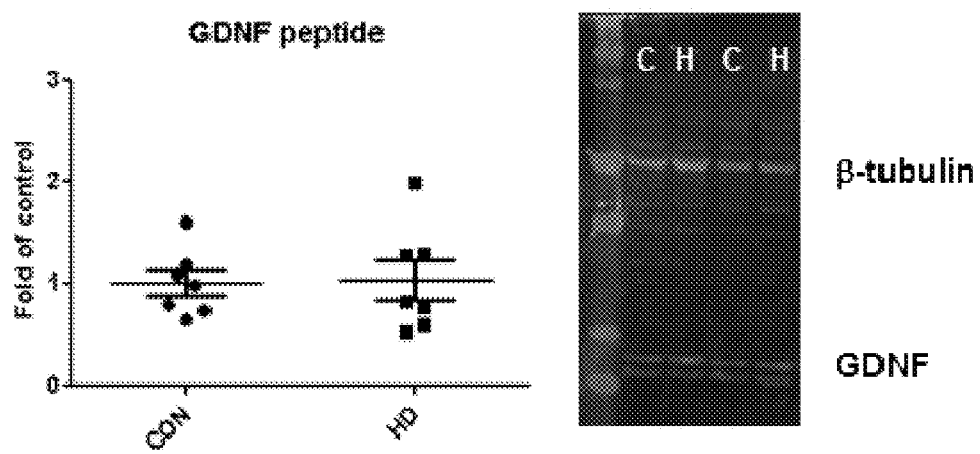
FIG. 5B shows expression of GDNF mature peptide levels in Huntington disease (HD) patients. Shown on the left is a scatter plot of HD MTG normalized by control. The Y axis is the fold change over control. The Western blot on the right shows GDNF mature peptide levels in MTG of control (C) and HD (H) subjects.
Figure 6A:
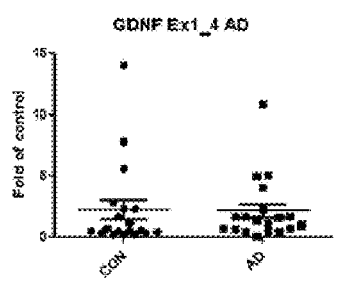
FIGS. 6A-6F are a series of graphs showing GDNF and GDNFOS isoform mRNA levels in AD, HD and control MTG. Shown are: (A) GDNF Ex1_4 in AD; (B) GDNFβ short in AD; (C) GDNFOS-1 in AD; (D) GDNF Ex2_4 in AD; (E) GDNF Ex2_4 in HD; and (F) GDNFαlong in AD.
Figure 6B:
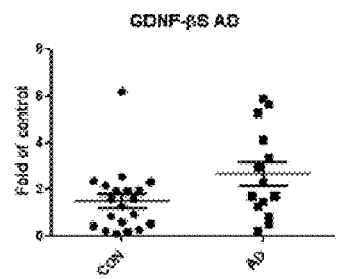
Figure 6C:
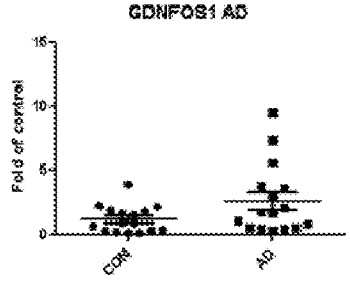
Figure 6D:
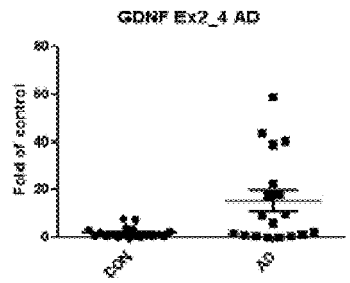
Figure 6E:
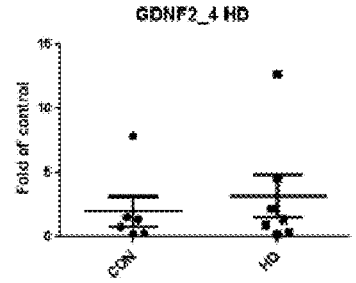
Figure 6F:
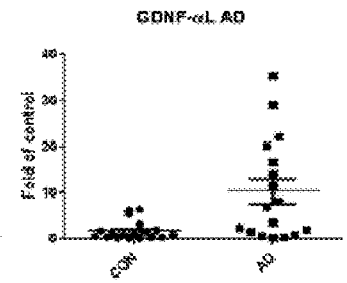

Primate-Specific GDNF Transcripts and Mature GDNF Peptide are Dysregulated in MTG of AD The RNA and protein qualities of the postmortem MTG samples of both controls and AD brains were tested by RNA integrity numbers (average RIN=5.04) and integrity of a single tubulin band on Western blot (FIG. 5A and FIG. 5B), respectively. A two-tailed Mann-Whitney for Gaussian approximation U-test showed that there were no significant changes (FIGS. 6A, 6B and 6C) in the exon 1 driven isoform, pre-(β)short-proGDNF transcript and GDNFOS transcript (Ex1_4: p=0.411; hGDNFβS: p=0.089 and GDNFOS-1: p=0.101, respectively) at the mRNA level, however, the primate exon 2 driven transcript (Ex2_4) and pre-(α)long-proGDNF transcript (hGDNFαL) encoding DNSP-11 mRNAs were significantly increased more than 10-fold (FIG. 6D and FIG. 6F) in AD MTG in comparison with the matched controls (Ex2_4: p=0.013 and hGDNFαL: p=0.003). The exon 3 driven isoform mRNA (Ex3_4) could not be detected in any of the MTG samples using RT-qPCR. An unpaired two-tailed Student t-test showed that the mature GDNF peptide of 15 and 16 kDa were found to be decreased by 50% (FIG. 5A) in AD MTG in comparison with that of controls (p=0.0241, t=2.368, df=32). No significant changes in GDNF isoform mRNA or mature peptide levels were found in the MTG of HD (FIG. 5B and FIG. 6E), further indication of the specificity for GDNF dysregulation in AD MTG.

Figure 8A:
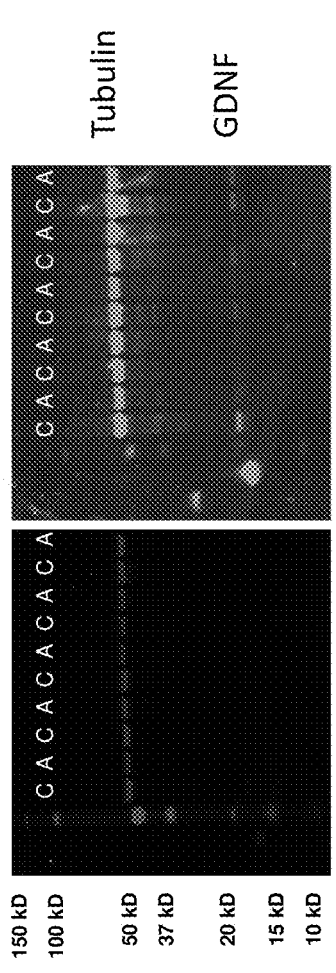
FIGS. 8A-8B are Western blots of Alzheimer's and Huntington's disease MTG samples. (A) Western blot using goat-anti-GDNF and rabbit-anti-tubulin antibodies and secondary donkey anti-goat IR CW800 and goat anti-rabbit IR CW680 antibodies (cross reaction of goat and rabbit secondary antibodies, shown by tubulin CW800 staining). C=control; A=Alzheimer's disease. (B) Western blot using goat-anti-GDNF and rabbit anti-tubulin antibodies and secondary donkey-anti-goat IR CW800 and donkey-anti-rabbit IR CW680 antibodies (no cross reaction of donkey secondary antibody, not shown by tubulin CW800 staining). C=control; H=Huntington's disease.
Figure 8B:
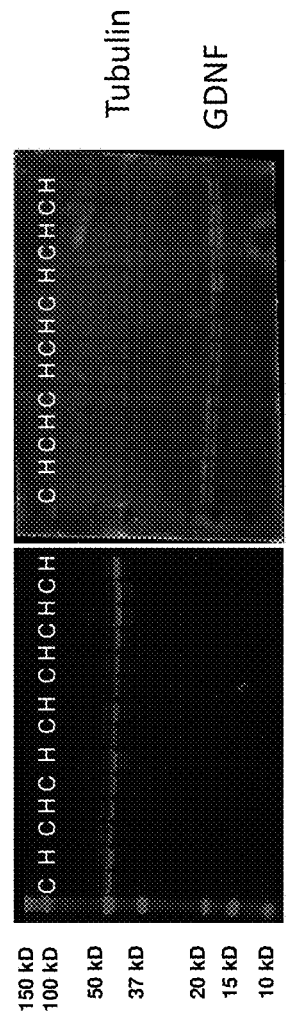
Figure 9A:
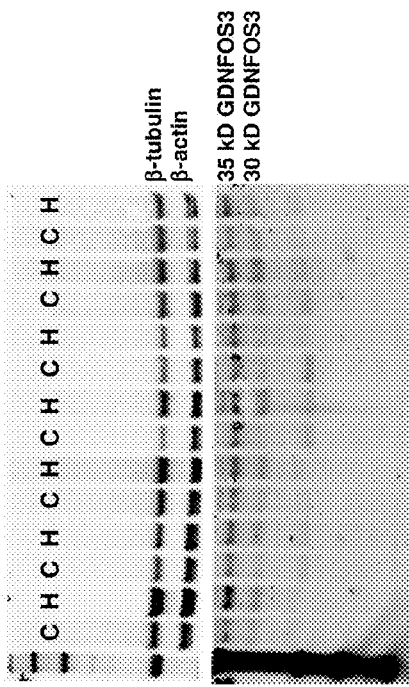
FIGS. 9A-9D show expression of GDNFOS-3 in Alzheimer's and Huntington's disease MTG samples. (A) Western blot using rabbit-anti-GDNFOS-3 and rabbit-anti-tubulin or actin antibodies and secondary donkey anti-rabbit IR CW680 antibodies. C=control; A=Alzheimer's disease. (B) Western blot using rabbit-anti-GDNFOS-3 and rabbit anti-tubulin and actin antibodies and secondary donkey-anti-rabbit IR CW680 antibodies. C=control; H=Huntington's disease. (C) Scatter plot of Alzheimer's disease MTG normalized by control. The Y axis is the fold change over control. (D) Scatter plot of Huntington's disease MTG normalized by control. The Y axis is the fold change over control.
Figure 9B:
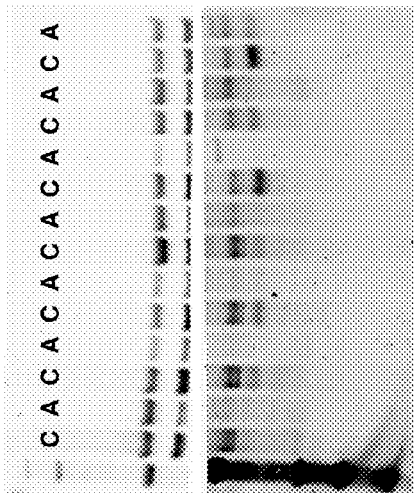
Figure 9C:
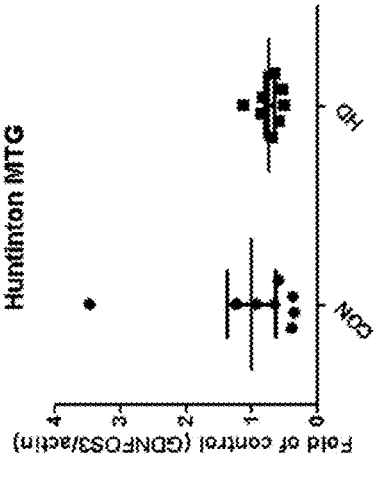
Figure 9D:
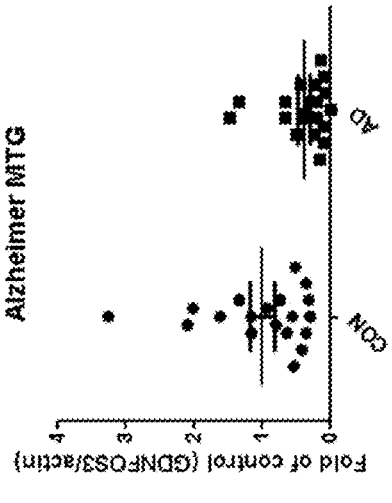
Figure 10:
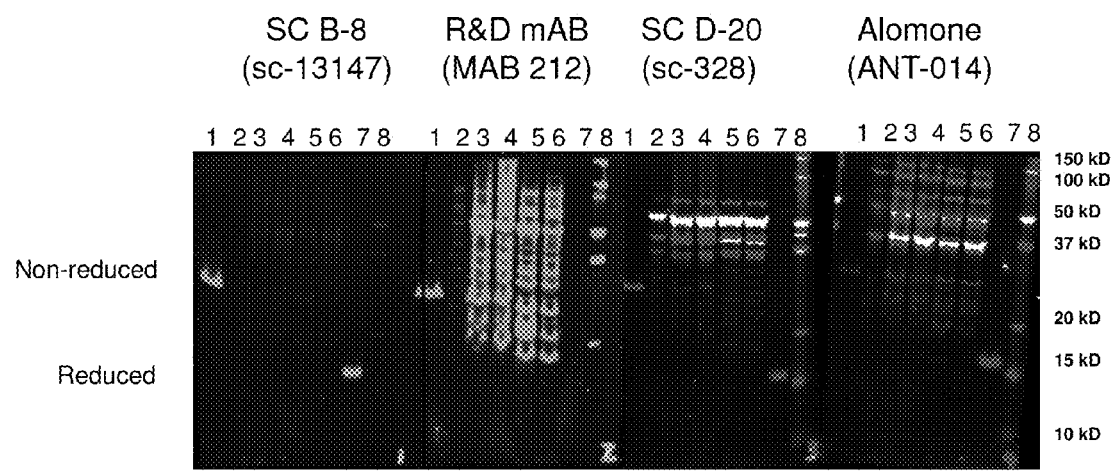
FIG. 10 is a Western blot of rat brain extracts using different commercial antibodies. Lanes are assigned as follows: 1—recombinant GDNF (non-reduced); 2—orbital frontal cortex (OFC; non-reduced); 3—ventral tegmental area (VTA; non-reduced); 4—striatum (Str; non-reduced); 5—VTA (reduced); 6—Str (reduced); 7—recombinant GDNF (reduced); and 8—precision molecular marker.

GDNF Protein and GDNFOS-3 Protein/Transcript is Reduced in Alzheimer's Disease MTG Western blots were performed to evaluate expression of GDNF and GDNFOS-3 protein in MTG of Alzheimer's disease and Huntington's disease patient samples (see FIGS. 8A-8B and 9A-9D). As shown in FIG. 8A, expression of GDNF protein is reduced in MTG of Alzheimer's disease samples relative to control samples. Similarly, expression of GDNFOS-3 protein is significantly reduced in MTG of Alzheimer's disease samples relative to control samples (FIG. 9A and FIG. 9C). A reduction in GDNFOS-3 peptide was not observed in middle frontal gyrus, which is generally less effected in Alzheimer's disease patients. Additional studies demonstrated that GDNFOS-3 transcript was also significantly reduced in MTG of Alzheimer's disease patients, but not in middle frontal gyrus.

Example 3

GDNFOS-3 Nonsynonymous Single Nucleotide Polymorphisms (SNPs)

Two SNPs have been identified in the GDNFOS-3 ORF. SNP rs6879269 results in a proline to arginine change at residue 75, which is a non-conservative amino acid change that would likely cause a GDNFOS-3 peptide functional change. The minor allele frequency of this SNP in Caucasians is 1.7%. The second SNP, rs6879269, results in a histidine to glutamine change at position 104, which is a conservative amino acid change that is not likely to cause a functional change in the GDNFOS-3 protein. The minor allele frequency of rs6879269 in Caucasians and Asians is 6.7% and 4.4%, respectively. One or both of the SNPs may be useful as genomic markers for human disease association. For example, the SNPs could be used to genotype a subject as susceptible to developing a neurodegenerative disease, such as Alzheimer's disease, Parkinson's disease, Huntington's disease or ALS.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A fusion protein comprising a glial cell line-derived neurotrophic factor opposite strand (GDNFOS) peptide and a heterologous protein, wherein the GDNFOS peptide comprises an amino acid sequence at least 90% identical to SEQ ID NO: 4 or at least 90% identical to residues 29-105 of SEQ ID NO: 4.

2. The fusion protein of claim 1, wherein the GDNFOS peptide comprises an amino acid sequence at least 95% identical to SEQ ID NO: 4 or at least 95% identical to residues 29-105 of SEQ ID NO: 4.

3. The fusion protein of claim 1, wherein the amino acid sequence of the GDNFOS peptide comprises or consists of SEQ ID NO: 4 or residues 29-105 of SEQ ID NO: 4.

4. A composition comprising the fusion protein of claim 1 and a pharmaceutically acceptable carrier.

5. The composition of claim 4, further comprising a glial cell line-derived neurotrophic factor protein.

6. The composition of claim 5, wherein the GDNF protein comprises human GDNF of SEQ ID NO: 45.

7. The composition of claim 4, further comprising the dopamine neuron-stimulating peptide-11 (DNSP-11) peptide of SEQ ID NO: 44.

8. The fusion protein of claim 1, wherein the GDNFOS peptide comprises an amino acid sequence at least 96% identical to SEQ ID NO: 4 or at least 96% identical to residues 29-105 of SEQ ID NO: 4.

9. The fusion protein of claim 1, wherein the GDNFOS peptide comprises an amino acid sequence at least 97% identical to SEQ ID NO: 4 or at least 97% identical to residues 29-105 of SEQ ID NO: 4.

10. The fusion protein of claim 1, wherein the GDNFOS peptide comprises an amino acid sequence at least 98% identical to SEQ ID NO: 4 or at least 98% identical to residues 29-105 of SEQ ID NO: 4.

11. The fusion protein of claim 1, wherein the GDNFOS peptide comprises an amino acid sequence at least 99% identical to SEQ ID NO: 4 or at least 99% identical to residues 29-105 of SEQ ID NO: 4.

12. The fusion protein of claim 1, wherein the heterologous protein is a reporter molecule, a protein tag or a carrier protein.

13. The fusion protein of claim 12, wherein the reporter molecule is a fluorescent protein or an enzyme.

14. The fusion protein of claim 12, wherein the protein tag is a His tag, FLAG tag, myc tag, chitin binding protein, maltose binding protein or glutathione-S-transferase.

15. The fusion protein of claim 12, wherein the carrier protein is keyhole limpet hemocyanin, bovine serum albumin, ovalbumin, thyroglobulin or tetanus toxoid.

16. A composition comprising a glial cell line-derived neurotrophic factor opposite strand (GDNFOS) peptide encapsulated in a biodegradable microparticle or nanoparticle, wherein the GDNFOS peptide comprises an amino acid sequence at least 90% identical to SEQ ID NO: 4 or at least 90% identical to residues 29-105 of SEQ ID NO: 4.

17. The composition of claim 16, wherein the biodegradable microparticle or nanoparticle comprises a poly(lactic acid), poly(glycolic acid), poly(D,L-lactic-co-glycolic acid) or poly(alkylcyanoacrylate) microparticle or nanoparticle.

18. The composition of claim 16, wherein the GDNFOS peptide comprises an amino acid sequence at least 95% identical to SEQ ID NO: 4 or at least 95% identical to residues 29-105 of SEQ ID NO: 4.

19. The composition of claim 16, wherein the amino acid sequence of the GDNFOS peptide comprises or consists of SEQ ID NO: 4 or residues 29-105 of SEQ ID NO: 4.

20. The composition of claim 16, further comprising a glial cell line-derived neurotrophic factor (GDNF) protein.

21. The composition of claim 20, wherein the GDNF protein comprises human GDNF of SEQ ID NO: 45 or the dopamine neuron-stimulating peptide-11 (DNSP-11) peptide of SEQ ID NO: 44.

* * * * *